US012558338B2

(12) United States Patent
Guo et al.

(10) Patent No.: US 12,558,338 B2
(45) Date of Patent: Feb. 24, 2026

(54) PHARMACEUTICAL COMPOSITION

(71) Applicant: SUNSHINE LAKE PHARMA CO., LTD., Guangdong (CN)

(72) Inventors: Binbin Guo, Dongguan (CN); Juan Li, Dongguan (CN); Ping Song, Dongguan (CN); Jiajun Guo, Dongguan (CN); Liuxiao Tu, Dongguan (CN); Fayin Tian, Dongguan (CN); Buwen Zhao, Dongguan (CN); Jinsong You, Dongguan (CN); Fangfang Huang, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 988 days.

(21) Appl. No.: 17/768,630

(22) PCT Filed: Oct. 14, 2020

(86) PCT No.: PCT/CN2020/120983

§ 371 (c)(1),
(2) Date: Apr. 13, 2022

(87) PCT Pub. No.: WO2021/073548

PCT Pub. Date: Apr. 22, 2021

(65) Prior Publication Data

US 2024/0299333 A1 Sep. 12, 2024

(30) Foreign Application Priority Data

Oct. 16, 2019 (CN) ......................... 201910984428.7
Jul. 24, 2020 (CN) ......................... 202010721215.8

(51) Int. Cl.

| | |
|---|---|
| *A61K 31/27* | (2006.01) |
| *A61K 9/00* | (2006.01) |
| *A61K 9/10* | (2006.01) |
| *A61K 9/19* | (2006.01) |
| *A61K 47/10* | (2017.01) |
| *A61K 47/12* | (2006.01) |
| *A61K 47/26* | (2006.01) |
| *A61K 47/32* | (2006.01) |
| *A61K 47/38* | (2006.01) |
| *A61K 47/44* | (2017.01) |

(52) U.S. Cl.

CPC ............ *A61K 31/27* (2013.01); *A61K 9/0019* (2013.01); *A61K 9/10* (2013.01); *A61K 9/19* (2013.01); *A61K 47/10* (2013.01); *A61K 47/12* (2013.01); *A61K 47/26* (2013.01); *A61K 47/32* (2013.01); *A61K 47/38* (2013.01); *A61K 47/44* (2013.01)

(58) Field of Classification Search

None

See application file for complete search history.

(56) References Cited

U.S. PATENT DOCUMENTS

| | | | |
|---|---|---|---|
| 2019/0144378 | A1 | 5/2019 | He et al. |
| 2019/0315679 | A1 | 10/2019 | Ye et al. |

FOREIGN PATENT DOCUMENTS

| | | | | |
|---|---|---|---|---|
| CN | 1539409 | A | | 10/2004 |
| CN | 104306330 | A | | 1/2015 |
| CN | 108261394 | A | * | 7/2018 |
| CN | 108969478 | A | | 12/2018 |
| CN | 109862887 | A | * | 6/2019 |
| CN | 110433131 | A | | 11/2019 |
| WO | 2009/156161 | A1 | | 12/2009 |
| WO | 2018/086534 | A1 | | 5/2018 |

OTHER PUBLICATIONS

Jan. 12, 2021 International Search Report issued in International Patent Application No. PCT/CN2020/120983.

Jan. 12, 2021 Written Opinion of the International Searching Authority issued in International Patent Application No. PCT/CN2020/120983.

* cited by examiner

*Primary Examiner* — Robert A Wax
*Assistant Examiner* — Kimberly Barber
(74) *Attorney, Agent, or Firm* — Oliff PLC

(57) ABSTRACT

A ((((1r,3R,5S,7r)-3,5-dimethyladamantan-1-yl)carbamoyl)oxy)-methyl benzoate injection preparation contains ((((1r,3R,5S,7r)-3,5-dimethyladamantan-1-yl)carbamoyl)oxy)-methyl benzoate, a suspension agent, a stabilizer, an osmotic pressure adjustment agent, a pH regulator and a solvent; and the preparation may be a ready-to-use liquid injection and may also be a lyophilized powder for injection. The preparation has noticeable slow-release effects after injection, so that the drug action time can be prolonged, the frequency of dose can be reduced, the compliance of patients can be enhanced, and bioavailability can be increased. A method for preparing the above-mentioned ((((1r,3R,5S,7r)-3,5-dimethyladamantan-1-yl)carbamoyl)oxy)-methyl benzoate injection preparation is simple, economical and suitable for industrial production.

20 Claims, 2 Drawing Sheets

PHARMACEUTICAL COMPOSITION

CROSS-REFERENCE TO RELATED APPLICATION

This is a U.S. national stage application of the International Patent Application No. PCT/CN2020/120983, filed on Oct. 14, 2020, which claims the priorities and benefits of Chinese Patent Application Nos. 201910984428.7 and 202010721215.8, filed with the State Intellectual Property Office of China on Oct. 16, 2019 and Jul. 24, 2020, respectively, which are incorporated herein by reference in their entirety.

FIELD OF THE INVENTION

The invention relates to the field of pharmaceutical formulation, in particular to a ((((1r,3R,5S,7r)-3,5-dimethyladamantan-1-yl)carbamoyl)oxy)methyl benzoate injection formulation.

BACKGROUND

Alzheimer's disease (AD) is one of the common diseases of the elderly, it is a chronic neurodegenerative disease characterized by memory loss and cognitive function loss as the main clinical features. As the population ages, the incidence of the disease continues to increase. About 20% of people over 80 have Alzheimer's disease. According to the clinical deterioration of cognitive function and physical function, the disease is divided into three stages: the first stage (1 to 3 years, mild dementia), the second stage (2 to 10 years, moderate dementia), and the third stage (8 to 12 years, severe dementia), patients with severe dementia are completely dependent on others, they have severe memory loss and cannot take care of themselves in daily life. They are incontinent, showing mutism, limb rigidity, positive pyramidal tract sign on physical examination, primitive reflexes such as strong grip, groping, and sucking, and eventually coma, which may cause death such as infection. Because the patients have problems in memory, judgment and thinking, the ability to take care of themselves in life is reduced, and the patients suffer great mental pain. In addition, the course of the disease lasts for a long time, which greatly increases the burden on the society and family.

Memantine is an excitatory amino acid receptor antagonist for the treatment of moderate to severe Alzheimer's dementia. At present, the oral administration products listed at home and abroad include memantine hydrochloride tablets, memantine hydrochloride solution, memantine hydrochloride sustained-release capsules. These dosage forms maintain short plasma concentrations, require frequent dosing, which increase patient non-compliance and adverse reactions. Due to the influence of patients' cognitive impairment and other symptoms, the ability to actively use drugs decreases, often leading to treatment failure.

At present, there is no long-acting injection of memantine (chemical name: 1-amino-3,5-dimethyladamantanamine, the structure is shown in the following formula C) and salt or ester thereof on the market, and there is a lack of research on parenteral formulations of memantine and salt thereof in the prior art. The structure of ((((1r,3R,5S,7r)-3,5-dimethyladamantan-1-yl)carbamoyl)oxy)methyl benzoate is shown in formula A, which is a prodrug obtained by memantine modification through esterification. Compared with memantine hydrochloride (chemical name: 1-amino-3,5-dimethyladamantanamine hydrochloride, the structure is shown in the following formula B), this compound has a significantly lower solubility and is almost insoluble in water. Through the slow dissolution of the drug in the tissue site, the speed of the drug entering the blood circulation is delayed, and the effect of sustained release in the body is achieved, so as to achieve the purpose of long-term treatment.

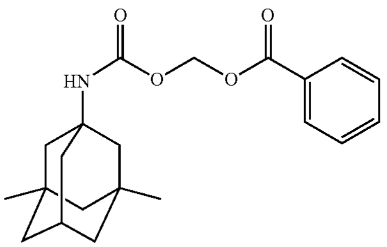

A

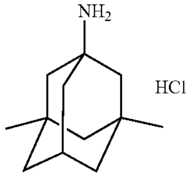

B

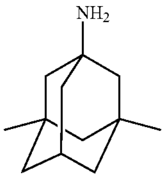

C

SUMMARY

Summary of the Invention

The first aspect of the present invention provides a ((((1r,3R,5S,7r)-3,5-dimethyladamantan-1-yl)carbamoyl)oxy)methyl benzoate injection formulation. In the formulation provided herein, the concentration of ((((1r,3R,5S,7r)-3,5-dimethyladamantan-1-yl)carbamoyl)oxy)methyl benzoate is high, the particle size is controllable, and a higher dose can be obtained within a limited injection volume to achieve long-term drug release. The formulation can be stored in a prefilled syringe in the form of suspension, or in a vial in the form of freeze-dried powder. The former can be used directly, and the latter can be used by intramuscular injection or subcutaneous injection after mixing with matching sterile water for injection to form a suspension. Compared with oral memantine tablets, the advantages of the formulation provided by the present invention include:

(1) API (pharmaceutical active ingredient) in the suspension exists as insoluble particles with low solubility. After injection, the drug has obvious sustained release effect, and can significantly reduce the time of administration, prolong drug action time, and improve patient compliance;

(2) The drug loading of the formulation is relatively high, and a dose for at least one week or longer can be obtained;

(3) The API particle size in the suspension is controllable and has good injectability;

(4) After the suspension is freeze-dried, it has good stability, which is beneficial to storage and transportation;

(5) The formulation has stable drug release, which can avoid the fluctuation of clinical indicators caused by missed doses.

The second aspect of the present invention provides a preparation method of ((((1r,3R,5S,7r)-3,5-dimethyladamantan-1-yl)carbamoyl)oxy)methyl benzoate injection formulation. The preparation method provided herein is simple and feasible, has good stability and high safety, and is suitable for industrial production. The preparation method can also add a freeze-drying step to prepare a ((((1r,3R,5S,7r)-3,5-dimethyladamantan-1-yl)carbamoyl)oxy)methyl benzoate freeze-dried formulation.

The third aspect of the present invention provides a method for treating Alzheimer's disease in a human in need thereof, wherein the method comprises administering to the human an injection of ((((1r,3R,5S,7r)-3,5-dimethyladamantan-1-yl)carbamoyl)oxy)methyl benzoate.

Definition of Terms

The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

The term "comprise" or "include" or "contain" is an open expression, it means comprising the contents disclosed herein, but don't exclude other contents.

In the context, all numbers disclosed herein are approximations, whether or not the word "about" is used. Based on the published values, each numerical value has a difference of less than ±10% or a reasonable difference considered by those skilled in the art, such as #1%, ±2%, ±3%, ±4% or ±5%.

The term "D[4,3]" refers to the volume weighted average measured by a Malvern Mastersizer 3000 Laser particle size analyzer.

The term "Dv10" refers to the particle size corresponding to the cumulative particle size volume distribution percentage of a sample reaching 10%, The term "Dv50" refers to the particle size corresponding to the cumulative particle size volume distribution percentage of a sample reaching 50%, the term "Dv90" refers to the particle size corresponding to the cumulative particle size volume distribution percentage of a sample reaching 90%.

LC/MS/MS refers to LC/MS.

"Sustained-release" refers to the sample is detected by LC/MS/MS analytical instrument, and the plasma concentration of memantine (1-amino-3,5-dimethyladamantan-amine) can be detected according to its detection limit.

Concentration "mg/mL" refers to milligram/milliliter, which means weight/volume. The volume is the volume of the suspension, including the suspension before freeze-drying, or the suspension after freeze-drying and reconstitution.

μm refers to micrometer, μL refers to microliter, L refers to liter, mm refers to millimeter, mL refers to milliliter, nm refers to nanometer, ng refers to nanogram, kg refers to kilogram, min refers to minute, d refers to day, Hz refers to hertz, g refers to gram, qs. refers to added to, mbar refers to millibar, V refers to volt, ° C. refers to degrees Celsius.

DETAILED DESCRIPTION OF THE INVENTION

Based on the deficiencies of the prior art, after in-depth investigation and research, the present invention provides a ((((1r,3R,5S,7r)-3,5-dimethyladamantan-1-yl)carbamoyl)oxy)methyl benzoate injection formulation. The formulation provided herein can be a suspension or a freeze-dried powder. The former can be used directly, and the latter can be use by intramuscular injection or subcutaneous injection after mixing with matching sterile water for injection to form a suspension. Compared with oral memantine tablets, the formulation provided herein has a higher drug load and can slowly and continuously release the drug after injection. It can obtain sustained release for at least 1 week or longer, significantly reduce the time of administration, and can avoid peak-to-valley fluctuation, thereby improving patient compliance and safety. The injection formulation provided herein has good stability and is convenient for storage and transportation; and when the formulation is in the form of a suspension, the particle size of ((((1r,3R,5S,7r)-3,5-dimethyladamantan-1-yl)carbamoyl)oxy)methyl benzoate in the suspension is controllable and the formulation has good injectability, which is beneficial to improve the bioavailability.

The invention provides a ((((1r,3R,5S,7r)-3,5-dimethyladamantan-1-yl)carbamoyl)oxy)methyl benzoate injection formulation, the Dv50 of ((((1r,3R,5S,7r)-3,5-dimethyladamantan-1-yl)carbamoyl)oxy)methyl benzoate can be 1.0 μm-20.0 μm. In some embodiments, the Dv50 of ((((1r,3R,5S,7r)-3,5-dimethyladamantan-1-yl)carbamoyl)oxy)methyl benzoate is 1.0 μm-15.0 μm, or 1.0 μm-10.0 μm, or 1.0 μm-5.0 μm, or 1.0 μm-2.0 μm, or 1.0 μm-3.0 μm, or 1.0 μm-4.0 μm, or 1.0 μm-6.0 μm, or 1.0 μm-7.0 μm, or 1.0 μm-8.0 μm, or 2.0 μm-5.0 μm, or 2.0 μm-8.0 μm, or 5.0 μm-8.0 μm, or 8.0 μm-15.0 μm. In some embodiments, the Dv50 of ((((1r,3R,5S,7r)-3,5-dimethyladamantan-1-yl)carbamoyl)oxy)methyl benzoate is 5.0 μm-10.0 μm; in some embodiments, the Dv50 of ((((1r,3R,5S,7r)-3,5-dimethyladamantan-1-yl)carbamoyl)oxy)methyl benzoate is 5.0 μm-15.0 μm; in some embodiments, the Dv50 of ((((1r,3R,5S,7r)-3,5-dimethyladamantan-1-yl)carbamoyl)oxy)methyl benzoate is 5.0 μm-20.0 μm; in some embodiments, the Dv50 of ((((1r,3R,5S,7r)-3,5-dimethyladamantan-1-yl)carbamoyl)oxy)methyl benzoate is 10.0 μm-15.0 μm; in some embodiments, the Dv50 of ((((1r,3R,5S,7r)-3,5-dimethyladamantan-1-yl)carbamoyl)oxy)methyl benzoate is 10.0 μm-20.0 μm; in some embodiments, the Dv50 of ((((1r,3R,5S,7r)-3,5-dimethyladamantan-1-yl)carbamoyl)oxy)methyl benzoate is 15.0 μm-20.0 μm; in some embodiments, the Dv50 of ((((1r,3R,5S,7r)-3,5-dimethyladamantan-1-yl)carbamoyl)oxy)methyl benzoate is 3.0 μm-7.0 μm.

For the ((((1r,3R,5S,7r)-3,5-dimethyladamantan-1-yl)carbamoyl)oxy)methyl benzoate injection formulation, the Dv10 of ((((1r,3R,5S,7r)-3,5-dimethyladamantan-1-yl)carbamoyl)oxy)methyl benzoate can be 0.1 μm-5.0 μm. In some embodiments, the Dv10 of ((((1r,3R,5S,7r)-3,5-dimethyladamantan-1-yl)carbamoyl)oxy)methyl benzoate is 1.0 μm-3.0 μm. In some embodiments, the Dv10 of ((((1r,3R,5S,7r)-3,5-dimethyladamantan-1-yl)carbamoyl)oxy)methyl benzoate is 1.0 μm-2.0 μm; in some embodiments, the Dv10 of ((((1r,3R,5S,7r)-3,5-dimethyladamantan-1-yl)carbamoyl)oxy)methyl benzoate is 1.0 μm-5.0 μm; in some embodiments, the Dv10 of ((((1r,3R,5S,7r)-3,5-dimethyladamantan-1-yl)carbamoyl)oxy)methyl benzoate is 2.0 μm-3.0 μm; in some embodiments, the Dv10 of ((((1r,3R,5S,7r)-3,5-dimethyladamantan-1-yl)carbamoyl)oxy)methyl benzoate is 2.0 μm-5.0 μm; in some embodiments, the Dv10 of ((((1r,3R,5S,7r)-3,5-dimethyladamantan-1-yl)carbamoyl)oxy)methyl benzoate is 3.0 μm-5.0 μm.

For the ((((1r,3R,5S,7r)-3,5-dimethyladamantan-1-yl)carbamoyl)oxy)methyl benzoate injection formulation, the Dv90 of ((((1r,3R,5S,7r)-3,5-dimethyladamantan-1-yl)carbamoyl)oxy)methyl benzoate can be 5.0 μm-60.0 μm. In some embodiments, the Dv90 of ((((1r,3R,5S,7r)-3,5-dimethyladamantan-1-yl)carbamoyl)oxy)methyl benzoate is 5.0 μm-20.0 μm. In some embodiments, the Dv90 of ((((1r,3R,5S,7r)-3,5-dimethyladamantan-1-yl)carbamoyl)oxy)methyl benzoate is 5.0 μm-10.0 μm; in some embodiments, the Dv90 of ((((1r,3R,5S,7r)-3,5-dimethyladamantan-1-yl)carbamoyl)oxy)methyl benzoate is 5.0 μm-30.0 μm; in some embodiments, the Dv90 of ((((1r,3R,5S,7r)-3,5-dimethyladamantan-1-yl)carbamoyl)oxy)methyl benzoate is 10.0 μm-20.0 μm; in some embodiments, the Dv90 of ((((1r,3R,5S,7r)-3,5-dimethyladamantan-1-yl)carbamoyl)oxy)methyl benzoate is 10.0 μm-30.0 μm; in some embodiments, the Dv90 of ((((1r,3R,5S,7r)-3,5-dimethyladamantan-1-yl)carbamoyl)oxy)methyl benzoate is 10.0 μm-60.0 μm; in some embodiments, the Dv90 of ((((1r,3R,5S,7r)-3,5-dimethyladamantan-1-yl)carbamoyl)oxy)methyl benzoate is 20.0 μm-30.0 μm; in some embodiments, the Dv90 of ((((1r,3R,5S,7r)-3,5-dimethyladamantan-1-yl)carbamoyl)oxy)methyl benzoate is 20.0 μm-60.0 μm; in some embodiments, the Dv90 of ((((1r,3R,5S,7r)-3,5-dimethyladamantan-1-yl)carbamoyl)oxy)methyl benzoate is 30.0 μm-60.0 μm.

In some embodiments, for the ((((1r,3R,5S,7r)-3,5-dimethyladamantan-1-yl)carbamoyl)oxy)methyl benzoate injection formulation, the Dv50 of ((((1r,3R,5S,7r)-3,5-dimethyladamantan-1-yl)carbamoyl)oxy)methyl benzoate is 1.0 μm-20.0 μm, the Dv10 is 0.1 μm-5.0 μm, the Dv90 is 5.0 μm-60.0 μm.

For the ((((1r,3R,5S,7r)-3,5-dimethyladamantan-1-yl)carbamoyl)oxy)methyl benzoate injection formulation, the D[4,3] of ((((1r,3R,5S,7r)-3,5-dimethyladamantan-1-yl)carbamoyl)oxy)methyl benzoate can be 1.0 μm-30.0 μm. In some embodiments, the D[4,3] of ((((1r,3R,5S,7r)-3,5-dimethyladamantan-1-yl)carbamoyl)oxy)methyl benzoate is 3.0 μm-20.0 μm. In some embodiments, the D[4,3] of ((((1r,3R,5S,7r)-3,5-dimethyladamantan-1-yl)carbamoyl)oxy)methyl benzoate is 1.0 μm-5.0 μm; in some embodiments, the D[4,3] of ((((1r,3R,5S,7r)-3,5-dimethyladamantan-1-yl)carbamoyl)oxy)methyl benzoate is 1.0 μm-10.0 μm; in some embodiments, the D[4,3] of ((((1r,3R,5S,7r)-3,5-dimethyladamantan-1-yl)carbamoyl)oxy)methyl benzoate is 1.0 μm-20.0 μm; in some embodiments, the D[4,3] of ((((1r,3R,5S,7r)-3,5-dimethyladamantan-1-yl)carbamoyl)oxy)methyl benzoate is 5.0 μm-10.0 μm; in some embodiments, the D[4,3] of ((((1r,3R,5S,7r)-3,5-dimethyladamantan-1-yl)carbamoyl)oxy)methyl benzoate is 5.0 μm-20.0 μm; in some embodiments, the D[4,3] of ((((1r,3R,5S,7r)-3,5-dimethyladamantan-1-yl)carbamoyl)oxy)methyl benzoate is 5.0 μm-30.0 μm; in some embodiments, the D[4,3] of ((((1r,3R,5S,7r)-3,5-dimethyladamantan-1-yl)carbamoyl)oxy)methyl benzoate is 10.0 μm-20.0 μm; in some embodiments, the D[4,3] of ((((1r,3R,5S,7r)-3,5-dimethyladamantan-1-yl)carbamoyl)oxy)methyl benzoate is 10.0 μm-30.0 μm; in some embodiments, the D[4,3] of ((((1r,3R,5S,7r)-3,5-dimethyladamantan-1-yl)carbamoyl)oxy)methyl benzoate is 20.0 μm-30.0 μm.

In some embodiments, for the ((((1r,3R,5S,7r)-3,5-dimethyladamantan-1-yl)carbamoyl)oxy)methyl benzoate injection formulation, the Dv50 of ((((1r,3R,5S,7r)-3,5-dimethyladamantan-1-yl)carbamoyl)oxy)methyl benzoate is 1.0 μm-20.0 μm, the Dv10 is 0.1 μm-5.0 μm, the Dv90 is 5.0 μm-60.0 μm, the D[4,3] is 1.0 μm-30.0 μm.

The ((((1r,3R,5S,7r)-3,5-dimethyladamantan-1-yl)carbamoyl)oxy)methyl benzoate injection formulation provided herein comprises: ((((1r,3R,5S,7r)-3,5-dimethyladamantan-1-yl)carbamoyl)oxy)methyl benzoate and a carrier.

In some embodiments, the ((((1r,3R,5S,7r)-3,5-dimethyladamantan-1-yl)carbamoyl)oxy)methyl benzoate injection formulation provided herein comprises:

(a) ((((1r,3R,5S,7r)-3,5-dimethyladamantan-1-yl)carbamoyl)oxy)methyl benzoate;
(b) a carrier; and
(c) water for injection.

In some embodiments, the ((((1r,3R,5S,7r)-3,5-dimethyladamantan-1-yl)carbamoyl)oxy)methyl benzoate injection formulation provided herein comprises:

(a) ((((1r,3R,5S,7r)-3,5-dimethyladamantan-1-yl)carbamoyl)oxy)methyl benzoate with the concentration of 105.0 mg/mL-300.0 mg/mL;
(b) a carrier; and optionally
(c) water for injection;

the formulation continues to release memantine for at least 1 week.

The carrier comprises at least one selected from stabilizer, suspending agent, pH adjuster, osmotic pressure adjuster, lyoprotectant.

In some embodiments, the carrier comprises stabilizer, and/or suspending agent, and/or osmotic pressure adjuster, and/or lyoprotectant, and/or pH adjuster.

The ((((1r,3R,5S,7r)-3,5-dimethyladamantan-1-yl)carbamoyl)oxy)methyl benzoate injection formulation provided herein can comprise a stabilizer.

The concentration of the stabilizer can be 5.0 mg/mL-48.0 mg/mL. In some embodiments, the concentration of the stabilizer is 10.0 mg/mL-35.0 mg/mL. In some embodiments, the concentration of the stabilizer is 6.0 mg/mL-10.0 mg/mL; in some embodiments, the concentration of the stabilizer is 6.0 mg/mL-15.0 mg/mL; in some embodiments, the concentration of the stabilizer is 6.0 mg/mL-20.0 mg/mL; in some embodiments, the concentration of the stabilizer is 6.0 mg/mL-30.0 mg/mL; in some embodiments, the concentration of the stabilizer is 6.0 mg/mL-35.0 mg/mL; in some embodiments, the concentration of the stabilizer is 10.0 mg/mL-15.0 mg/mL; in some embodiments, the concentration of the stabilizer is 10.0 mg/mL-20.0 mg/mL; in some embodiments, the concentration of the stabilizer is 10.0 mg/mL-30.0 mg/mL; in some embodiments, the concentration of the stabilizer is 10.0 mg/mL-35.0 mg/mL; in some embodiments, the concentration of the stabilizer is 10.0 mg/mL-48.0 mg/mL; in some embodiments, the concentration of the stabilizer is 15.0 mg/mL-20.0 mg/mL; in some embodiments, the concentration of the stabilizer is 15.0 mg/mL-30.0 mg/mL; in some embodiments, the concentration of the stabilizer is 15.0 mg/mL-35.0 mg/mL; in some embodiments, the concentration of the stabilizer is 15.0 mg/mL-48.0 mg/mL; in some embodiments, the concentration of the stabilizer is 20.0 mg/mL-30.0 mg/mL; in some embodiments, the concentration of the stabilizer is 20.0 mg/mL-35.0 mg/mL; in some embodiments, the concentration of the stabilizer is 20.0 mg/mL-48.0 mg/mL; in some embodiments, the concentration of the stabilizer is 30.0 mg/mL-35.0 mg/mL; in some embodiments, the concentration of the stabilizer is 30.0 mg/mL-48.0 mg/mL; in some embodiments, the concentration of the stabilizer is 35.0 mg/mL-48.0 mg/mL; in some embodiments, the concentration of the stabilizer is 5.0 mg/mL-25.0 mg/mL. In some embodiments, the concentration of the stabilizer is 7.9 mg/mL, 14.5 mg/mL, 15.0 mg/mL, 17.0 mg/mL, 20.0 mg/mL, 30.0 mg/mL or 35.0 mg/mL.

The stabilizer comprises at least one selected from Tween 20, Tween 60, Tween 80, Span 20, lecithin, poloxamer 188, poloxamer 338, poloxamer 407 and 15-hydroxystearate polyethylene glycol. In some embodiments, the stabilizer is Tween 80. In some embodiments, the stabilizer is a combination of Tween 80 and Span 20. In some embodiments, the stabilizer is a combination of Tween 20 and Span 20. In some embodiments, the stabilizer is poloxamer 338. In some embodiments, the stabilizer is poloxamer 188.

The concentration of the Tween 80 can be 2.0 mg/mL-30.0 mg/mL. In some embodiments, the concentration of the Tween 80 is 5.0 mg/mL-30.0 mg/mL, or 5.0 mg/ml-15.0 mg/mL, or 10.0 mg/mL-20.0 mg/mL. In some embodiments, the concentration of the Tween 80 is 5.0 mg/mL-10.0 mg/mL; in some embodiments, the concentration of the Tween 80 is 5.0 mg/ml-20.0 mg/mL; in some embodiments, the concentration of the Tween 80 is 10.0 mg/mL-15.0 mg/mL; in some embodiments, the concentration of the Tween 80 is 10.0 mg/mL-30.0 mg/mL; in some embodiments, the concentration of the Tween 80 is 15.0 mg/mL-20.0 mg/mL; in some embodiments, the concentration of the Tween 80 is 15.0 mg/mL-30.0 mg/mL; in some embodiments, the concentration of the Tween 80 is 20.0 mg/mL-30.0 mg/mL. In some embodiments, the concentration of the Tween 80 is 5.5 mg/mL, 10.0 mg/mL, 15.0 mg/mL, 20.0 mg/mL or 30.0 mg/mL.

The concentration of the Span 20 can be 0 mg/mL-15.0 mg/mL. In some embodiments, the concentration of the Span 20 is 2.5 mg/mL-10.0 mg/mL or 5.0 mg/mL-12.50 mg/mL. In some embodiments, the concentration of the Span 20 is 1.0 mg/mL-2.5 mg/mL; in some embodiments, the concentration of the Span 20 is 1.0 mg/mL-5.0 mg/mL; in some embodiments, the concentration of the Span 20 is 1.0 mg/mL-10.0 mg/mL; in some embodiments, the concentration of the Span 20 is 1.0 mg/mL-12.5 mg/mL; in some embodiments, the concentration of the Span 20 is 2.5 mg/mL-5.0 mg/mL; in some embodiments, the concentration of the Span 20 is 2.5 mg/mL-12.5 mg/mL; in some embodiments, the concentration of the Span 20 is 2.5 mg/mL-18 mg/mL; in some embodiments, the concentration of the Span 20 is 5.0 mg/mL-10.0 mg/mL; in some embodiments, the concentration of the Span 20 is 5.0 mg/mL-18 mg/mL; in some embodiments, the concentration of the Span 20 is 10.0 mg/mL-12.5 mg/mL; in some embodiments, the concentration of the Span 20 is 10.0 mg/mL-18.0 mg/mL. In some embodiments, the concentration of the Span 20 is 2.5 mg/mL or 5.0 mg/mL.

In some embodiments, the stabilizer is a combination of Tween 80 and Span 20, and the concentration ratio of Tween 80 to Span 20 is 1:1-6:1. In some embodiments, the concentration ratio of Tween 80 to Span 20 is 2:1; in some embodiments, the concentration ratio of Tween 80 to Span 20 is 2.4:1; in some embodiments, the concentration ratio of Tween 80 to Span 20 is 3:1; in some embodiments, the concentration ratio of Tween 80 to Span 20 is 4:1; in some embodiments, the concentration ratio of Tween 80 to Span 20 is 4.8:1; in some embodiments, the concentration ratio of Tween 80 to Span 20 is 6:1.

The ((((1r,3R,5S,7r)-3,5-dimethyladamantan-1-yl)carbamoyl)oxy)methyl benzoate injection formulation provided herein can comprise a suspending agent.

The concentration of the suspending agent can be 0.35 mg/mL-125.0 mg/mL. In some embodiments, the concentration of the suspending agent is 40.0 mg/mL-100.0 mg/mL or 50.0 mg/mL-120.0 mg/mL. In some embodiments, the concentration of the suspending agent is 40.0 mg/mL-60.0 mg/mL; in some embodiments, the concentration of the suspending agent is 40.0 mg/mL-80.0 mg/mL; in some embodiments, the concentration of the suspending agent is 40.0 mg/mL-125.0 mg/mL; in some embodiments, the concentration of the suspending agent is 60.0 mg/mL-80.0 mg/mL; in some embodiments, the concentration of the suspending agent is 60.0 mg/mL-100.0 mg/mL; in some embodiments, the concentration of the suspending agent is 60.0 mg/mL-125.0 mg/mL; in some embodiments, the concentration of the suspending agent is 80.0 mg/mL-100.0 mg/mL; in some embodiments, the concentration of the suspending agent is 80.0 mg/mL-125.0 mg/mL; in some embodiments, the concentration of the suspending agent is 100.0 mg/mL-125.0 mg/mL; in some embodiments, the concentration of the suspending agent is 0.35 mg/mL-2.0 mg/mL; in some embodiments, the concentration of the suspending agent is 0.35 mg/mL-5.0 mg/mL; in some embodiments, the concentration of the suspending agent is 0.35 mg/mL-20.0 mg/mL. In some embodiments, the concentration of the suspending agent is 10.0 mg/mL, 40.0 mg/mL, 60.0 mg/mL, 80.0 mg/mL or 100.0 mg/mL.

The suspending agent comprises at least one selected from dextran, gelatin, hydroxypropyl methylcellulose, methylcellulose, gum arabic, polyethylene glycol 3350, polyethylene glycol 4000, polyethylene glycol 6000, sodium carboxymethyl cellulose and polyvinylpyrrolidone. In some embodiments, the suspending agent is polyethylene glycol 4000; in some embodiments, the suspending agent is polyethylene glycol 3350; in some embodiments, the suspending agent is polyethylene glycol 6000; in some embodiments, the suspending agent is sodium carboxymethyl cellulose; in some embodiments, the suspending agent is polyvinylpyrrolidone K12; in some embodiments, the suspending agent is polyvinylpyrrolidone K30.

In some embodiments, the concentration of the suspending agent polyethylene glycol 4000 is 35.0 mg/mL-125.0 mg/mL. In some embodiments, the concentration of the suspending agent polyethylene glycol 4000 is 50.0 mg/mL-120.0 mg/mL. In some embodiments, the concentration of the suspending agent polyethylene glycol 4000 is 40.0 mg/mL-60.0 mg/mL; in some embodiments, the concentration of the suspending agent polyethylene glycol 4000 is 40.0 mg/mL-80.0 mg/mL; in some embodiments, the concentration of the suspending agent polyethylene glycol 4000 is 40.0 mg/mL-125.0 mg/mL; in some embodiments, the concentration of the suspending agent polyethylene glycol 4000 is 60.0 mg/mL-80.0 mg/mL; in some embodiments, the concentration of the suspending agent polyethylene glycol 4000 is 60.0 mg/mL-100.0 mg/mL; in some embodiments, the concentration of the suspending agent polyethylene glycol 4000 is 60.0 mg/mL-125.0 mg/mL; in some embodiments, the concentration of the suspending agent polyethylene glycol 4000 is 80.0 mg/mL-100.0 mg/mL; in some embodiments, the concentration of the suspending agent polyethylene glycol 4000 is 80.0 mg/mL-125.0 mg/mL; in some embodiments, the concentration of the suspending agent polyethylene glycol 4000 is 100.0 mg/mL-125.0 mg/mL. In some embodiments, the concentration of the suspending agent polyethylene glycol 4000 is 40.0 mg/mL, 60.0 mg/mL, 80.0 mg/mL or 100.0 mg/mL.

The ((((1r,3R,5S,7r)-3,5-dimethyladamantan-1-yl)carbamoyl)oxy)methyl benzoate injection formulation provided herein can further comprise a pH adjuster.

The pH adjuster comprises at least one selected from hydrochloric acid, sodium hydroxide, phosphoric acid and its salts, tartaric acid and its salts, acetic acid and its salts, citric acid and its salts, carbonic acid and its salts. In some embodiments, the pH adjuster is sodium hydroxide; in some embodiments, the pH adjuster is phosphoric acid and its salts; in some embodiments, the pH adjuster is citric acid and its salts.

In some embodiments, the ((((1r,3R,5S,7r)-3,5-dimethyladamantan-1-yl)carbamoyl)oxy)methyl benzoate injection formulation comprises a stabilizer and a suspending agent.

In some embodiments, the ((((1r,3R,5S,7r)-3,5-dimethyladamantan-1-yl)carbamoyl)oxy)methyl benzoate injection formulation comprises a suspending agent and a pH adjuster.

In some embodiments, the ((((1r,3R,5S,7r)-3,5-dimethyladamantan-1-yl)carbamoyl)oxy)methyl benzoate injection formulation comprises a stabilizer and a pH adjuster.

In some embodiments, the ((((1r,3R,5S,7r)-3,5-dimethyladamantan-1-yl)carbamoyl)oxy)methyl benzoate injection formulation comprises a stabilizer, a suspending agent and a pH adjuster.

The ((((1r,3R,5S,7r)-3,5-dimethyladamantan-1-yl)carbamoyl)oxy)methyl benzoate injection formulation provided herein can comprise an osmotic pressure adjuster.

The ((((1r,3R,5S,7r)-3,5-dimethyladamantan-1-yl)carbamoyl)oxy)methyl benzoate injection formulation provided herein can comprise a lyoprotectant.

In some embodiments, the ((((1r,3R,5S,7r)-3,5-dimethyladamantan-1-yl)carbamoyl)oxy)methyl benzoate injection formulation comprises a stabilizer, and/or a suspending agent, and/or an osmotic pressure adjuster, and/or a lyoprotectant, and/or a pH adjuster.

In some embodiments, the ((((1r,3R,5S,7r)-3,5-dimethyladamantan-1-yl)carbamoyl)oxy)methyl benzoate injection formulation comprises a stabilizer, and/or a suspending agent.

In some embodiments, the ((((1r,3R,5S,7r)-3,5-dimethyladamantan-1-yl)carbamoyl)oxy)methyl benzoate injection formulation comprises a stabilizer, a suspending agent, a pH adjuster and an osmotic pressure adjuster.

In some embodiments, the ((((1r,3R,5S,7r)-3,5-dimethyladamantan-1-yl)carbamoyl)oxy)methyl benzoate injection formulation comprises a stabilizer, a suspending agent, an osmotic pressure adjuster and a lyoprotectant.

In some embodiments, the ((((1r,3R,5S,7r)-3,5-dimethyladamantan-1-yl)carbamoyl)oxy)methyl benzoate injection formulation comprises a stabilizer, a suspending agent and a pH adjuster.

In some embodiments, the ((((1r,3R,5S,7r)-3,5-dimethyladamantan-1-yl)carbamoyl)oxy)methyl benzoate injection formulation comprises a stabilizer and an osmotic pressure adjuster.

In some embodiments, the ((((1r,3R,5S,7r)-3,5-dimethyladamantan-1-yl)carbamoyl)oxy)methyl benzoate injection formulation comprises a stabilizer, a suspending agent and an osmotic pressure adjuster.

In some embodiments, the ((((1r,3R,5S,7r)-3,5-dimethyladamantan-1-yl)carbamoyl)oxy)methyl benzoate injection formulation comprises a stabilizer, a suspending agent and a lyoprotectant.

The osmotic pressure adjuster comprises at least one selected from anhydrous disodium hydrogen phosphate, citric acid monohydrate, sodium chloride, glucose, glycerol and citric acid.

The lyoprotectant comprises at least one selected from polyethylene glycol 3350, polyethylene glycol 4000, mannitol, sorbitol, glucose, sucrose, lactose, dextran, trehalose and glycine. In some embodiments, the lyoprotectant is polyethylene glycol 3350. In some embodiments, the lyoprotectant is polyethylene glycol 4000.

The concentration of the lyoprotectant can be 50.0 mg/mL-150.0 mg/mL. In some embodiments, the concentration of the lyoprotectant is 80.0 mg/mL-125.0 mg/mL. In some embodiments, the concentration of the lyoprotectant is 50.0 mg/mL-80.0 mg/ml; in some embodiments, the concentration of the lyoprotectant is 50.0 mg/mL-100.0 mg/mL; in some embodiments, the concentration of the lyoprotectant is 50.0 mg/mL-125.0 mg/mL; in some embodiments, the concentration of the lyoprotectant is 80.0 mg/mL-100.0 mg/mL; in some embodiments, the concentration of the lyoprotectant is 80.0 mg/mL-150.0 mg/mL; in some embodiments, the concentration of the lyoprotectant is 100.0 mg/mL-125.0 mg/mL; in some embodiments, the concentration of the lyoprotectant is 100.0 mg/mL-150.0 mg/mL; in some embodiments, the concentration of the lyoprotectant is 125.0 mg/mL-150.0 mg/mL. In some embodiments, the concentration of the lyoprotectant is 80.0 mg/mL, 90.0 mg/mL, 100.0 mg/mL or 125.0 mg/mL.

The ((((1r,3R,5S,7r)-3,5-dimethyladamantan-1-yl)carbamoyl)oxy)methyl benzoate injection formulation provided herein has a high drug load, wherein the concentration of the ((((1r,3R,5S,7r)-3,5-dimethyladamantan-1-yl)carbamoyl)oxy)methyl benzoate can be 105.0 mg/mL-300.0 mg/mL. In some embodiments, in the injection formulation, the concentration of the ((((1r,3R,5S,7r)-3,5-dimethyladamantan-1-yl)carbamoyl)oxy)methyl benzoate is 125.0 mg/mL-250.0 mg/mL. In some embodiments, the concentration of the ((((1r,3R,5S,7r)-3,5-dimethyladamantan-1-yl)carbamoyl)oxy)methyl benzoate is 105.0 mg/mL-150.0 mg/mL; in some embodiments, the concentration of the ((((1r,3R,5S,7r)-3,5-dimethyladamantan-1-yl)carbamoyl)oxy)methyl benzoate is 105.0 mg/mL-200.0 mg/mL; in some embodiments, the concentration of the ((((1r,3R,5S,7r)-3,5-dimethyladamantan-1-yl)carbamoyl)oxy)methyl benzoate is 105.0 mg/mL-250.0 mg/mL; in some embodiments, the concentration of the ((((1r,3R,5S,7r)-3,5-dimethyladamantan-1-yl)carbamoyl)oxy)methyl benzoate is 150.0 mg/mL-200.0 mg/mL; in some embodiments, the concentration of the ((((1r,3R,5S,7r)-3,5-dimethyladamantan-1-yl)carbamoyl)oxy)methyl benzoate is 150.0 mg/mL-250.0 mg/mL; in some embodiments, the concentration of the ((((1r,3R,5S,7r)-3,5-dimethyladamantan-1-yl)carbamoyl)oxy)methyl benzoate is 150.0 mg/mL-300.0 mg/mL; in some embodiments, the concentration of the ((((1r,3R,5S,7r)-3,5-dimethyladamantan-1-yl)carbamoyl)oxy)methyl benzoate is 200.0 mg/mL-250.0 mg/mL; in some embodiments, the concentration of the ((((1r,3R,5S,7r)-3,5-dimethyladamantan-1-yl)carbamoyl)oxy)methyl benzoate is 200.0 mg/mL-300.0 mg/mL; in some embodiments, the concentration of the ((((1r,3R,5S,7r)-3,5-dimethyladamantan-1-yl)carbamoyl)oxy)methyl benzoate is 250.0 mg/mL-300.0 mg/mL. In some embodiments, in the injection formulation, the concentration of the ((((1r,3R,5S,7r)-3,5-dimethyladamantan-1-yl)carbamoyl)oxy)methyl benzoate is 100 mg/mL, 125 mg/mL, 150.0 mg/mL, 200.0 mg/mL, 250.0 mg/mL or 300.0 mg/mL. In some embodiments, in the injection formulation, the concentration of the ((((1r,3R,5S,7r)-3,5-dimethyladamantan-1-yl)carbamoyl)oxy)methyl benzoate is 125.0 mg/mL, which is beneficial to obtain a formulation with better bioavailability.

The pH of the ((((1r,3R,5S,7r)-3,5-dimethyladamantan-1-yl)carbamoyl)oxy)methyl benzoate injection formulation is 6.0-9.0. In some embodiments, the pH of the formulation is 6.5-7.5, 6.5-8.0, 7.0-8.0 or 6.0-7.0. In some embodiments, the pH of the formulation is 7.0-7.5. In some embodiments, the pH of the formulation is 6.5-7.0.

After the injection of the ((((1r,3R,5S,7r)-3,5-dimethyladamantan-1-yl)carbamoyl)oxy)methyl benzoate injection formulation provided herein, it continues to release memantine for at least 1 week.

The ((((1r,3R,5S,7r)-3,5-dimethyladamantan-1-yl)carbamoyl)oxy)methyl benzoate injection formulation provided herein can be in the form of a suspension, wherein the Dv50 of ((((1r,3R,5S,7r)-3,5-dimethyladamantan-1-yl)carbamoyl)oxy)methyl benzoate is 1.0 μm-20.0 μm, and the formulation continues to release memantine for at least 2 weeks, up to 4 weeks or more, such as up to 6 weeks.

The ((((1r,3R,5S,7r)-3,5-dimethyladamantan-1-yl)carbamoyl)oxy)methyl benzoate injection formulation provided herein can be in the form of a suspension, wherein the concentration of the ((((1r,3R,5S,7r)-3,5-dimethyladamantan-1-yl)carbamoyl)oxy)methyl benzoate is 105.0 mg/mL-300.0 mg/mL, and the formulation continues to release memantine for at least 2 weeks, up to 4 weeks or more, such as up to 6 weeks.

The ((((1r,3R,5S,7r)-3,5-dimethyladamantan-1-yl)carbamoyl)oxy)methyl benzoate injection formulation provided herein can be a ready-to-use liquid injection or a freeze-dried formulation; the freeze-dried formulation needs to be reconstituted with water for injection before use. In some embodiments, the formulation is a ready-to-use liquid injection formulation, and in some embodiments, the formulation is a freeze-dried powder injection.

In some embodiments, the ((((1r,3R,5S,7r)-3,5-dimethyladamantan-1-yl)carbamoyl)oxy)methyl benzoate injection formulation is a freeze-dried formulation, the freeze-dried formulation is in the form of a cake.

In some embodiments, the pH of the ((((1r,3R,5S,7r)-3,5-dimethyladamantan-1-yl)carbamoyl)oxy)methyl benzoate freeze-dried formulation is 6.0-9.0. In some embodiments, the pH of the ((((1r,3R,5S,7r)-3,5-dimethyladamantan-1-yl)carbamoyl)oxy)methyl benzoate freeze-dried formulation is 6.5-7.5, 6.5-8.0, 7.0-8.0 or 6.0-7.0. In some embodiments, the pH of the ((((1r,3R,5S,7r)-3,5-dimethyladamantan-1-yl)carbamoyl)oxy)methyl benzoate freeze-dried formulation is 7.0-7.5. In some embodiments, the pH of the ((((1r,3R,5S,7r)-3,5-dimethyladamantan-1-yl)carbamoyl)oxy)methyl benzoate freeze-dried formulation is 6.5-7.0.

In some embodiments, the ((((1r,3R,5S,7r)-3,5-dimethyladamantan-1-yl)carbamoyl)oxy)methyl benzoate injection formulation comprises:

(a) ((((1r,3R,5S,7r)-3,5-dimethyladamantan-1-yl)carbamoyl)oxy)methyl benzoate;

(b) a stabilizer selected from Tween 80, poloxamer 188, poloxamer 338, poloxamer 407, and a combination of Tween 80 and Span 20; and/or (c) a suspending agent selected from polyethylene glycol 4000, polyethylene glycol 3350, sodium carboxymethyl cellulose and polyvinylpyrrolidone.

In some embodiments, the ((((1r,3R,5S,7r)-3,5-dimethyladamantan-1-yl)carbamoyl)oxy)methyl benzoate injection formulation comprises:

(a) ((((1r,3R,5S,7r)-3,5-dimethyladamantan-1-yl)carbamoyl)oxy)methyl benzoate with the concentration of 105.0 mg/mL-300.0 mg/mL;

(b) a stabilizer selected from Tween 80, poloxamer 188, poloxamer 338, poloxamer 407, and a combination of Tween 80 and Span 20, the concentration of the stabilizer is 5.0 mg/mL-48.0 mg/mL; and/or (c) a suspending agent selected from polyethylene glycol 4000, polyethylene glycol 3350, sodium carboxymethyl cellulose and polyvinylpyrrolidone, the concentration of the suspending agent is 0.35 mg/mL-125.0 mg/mL.

In some embodiments, the ((((1r,3R,5S,7r)-3,5-dimethyladamantan-1-yl)carbamoyl)oxy)methyl benzoate injection formulation comprises:

(a) ((((1r,3R,5S,7r)-3,5-dimethyladamantan-1-yl)carbamoyl)oxy)methyl benzoate with the concentration of 105.0 mg/mL-300.0 mg/mL;

(b) a combination of Tween 80 and Span 20, the concentration of the combination is 6.0 mg/mL-48.0 mg/mL; and/or (c) polyethylene glycol 4000 with the concentration of 35.0 mg/mL-125.0 mg/mL; optionally comprises a pH adjuster.

In some embodiments, the ((((1r,3R,5S,7r)-3,5-dimethyladamantan-1-yl)carbamoyl)oxy)methyl benzoate injection formulation comprises:

(a) ((((1r,3R,5S,7r)-3,5-dimethyladamantan-1-yl)carbamoyl)oxy)methyl benzoate with the concentration of 125.0 mg/mL-250.0 mg/mL;

(b) polyethylene glycol 4000 with the concentration of 50.0 mg/mL-120.0 mg/mL; and/or (c) a combination of Tween 80 and Span 20 with the concentration of 5.0 mg/mL-25.0 mg/mL;

optionally comprises a pH adjuster.

In some embodiments, the ((((1r,3R,5S,7r)-3,5-dimethyladamantan-1-yl)carbamoyl)oxy)methyl benzoate injection formulation comprises:

(a) ((((1r,3R,5S,7r)-3,5-dimethyladamantan-1-yl)carbamoyl)oxy)methyl benzoate with the concentration of 125.0 mg/ml;

(b) a combination of Tween 80 and Span 20 with the concentration of 8.0 mg/mL;

(c) polyethylene glycol 4000 with the concentration of 100.0 mg/mL.

In some embodiments, the ((((1r,3R,5S,7r)-3,5-dimethyladamantan-1-yl)carbamoyl)oxy)methyl benzoate injection formulation comprises:

(a) ((((1r,3R,5S,7r)-3,5-dimethyladamantan-1-yl)carbamoyl)oxy)methyl benzoate with the concentration of 250.0 mg/ml;

(b) a combination of Tween 80 and Span 20 with the concentration of 25.0 mg/ml;

(c) polyethylene glycol 4000 with the concentration of 120.0 mg/mL.

In another aspect, provided herein is a method for preparing any one of the above ((((1r,3R,5S,7r)-3,5-dimethyladamantan-1-yl)carbamoyl)oxy)methyl benzoate injection formulations.

A preparation of ((((1r,3R,5S,7r)-3,5-dimethyladamantan-1-yl)carbamoyl)oxy)methyl benzoate formulation, comprising the following steps:

(a) mixing the stabilizer and water, optionally, adding a suspending agent;

(b) adding ((((1r,3R,5S,7r)-3,5-dimethyladamantan-1-yl)carbamoyl)oxy)methyl benzoate to obtain a suspension;

(c) optionally, adjusting pH with a pH adjuster and then making constant volume;

(d) grinding the above suspension to obtain the final suspension.

In some embodiments, the preparation of ((((1r,3R,5S,7r)-3,5-dimethyladamantan-1-yl)carbamoyl)oxy)methyl benzoate formulation, comprising the following steps:

(a) mixing the stabilizer, suspending agent and water, optionally, adding a pH adjuster and an osmotic pressure adjuster;

(b) adding ((((1r,3R,5S,7r)-3,5-dimethyladamantan-1-yl)carbamoyl)oxy)methyl benzoate to obtain a suspension;

(c) optionally, adjusting pH at 6.0-9.0 with a pH adjuster and then making constant volume;

(d) grinding the above suspension to obtain the final suspension.

In some embodiments, the above suspension is ground with a ball mill.

In some embodiments, the preparation of ((((1r,3R,5S,7r)-3,5-dimethyladamantan-1-yl)carbamoyl)oxy)methyl benzoate formulation, comprising the following steps:

(a) mixing the Tween 80, Span 20 and water, optionally, adding a pH adjuster and an osmotic pressure adjuster;

(b) adding polyethylene glycol 4000;

(c) adding ((((1r,3R,5S,7r)-3,5-dimethyladamantan-1-yl)carbamoyl)oxy)methyl benzoate to obtain a suspension, adjusting pH at 6.5-7.5 and then making constant volume;

(d) grinding the above suspension with a planetary ball mill to obtain the final suspension.

The preparation of ((((1r,3R,5S,7r)-3,5-dimethyladamantan-1-yl)carbamoyl)oxy)methyl benzoate formulation provided herein can use wet grinding technology, and the grinding bead material is zirconia with good compatibility.

The preparation of ((((1r,3R,5S,7r)-3,5-dimethyladamantan-1-yl)carbamoyl)oxy)methyl benzoate injection provided herein can further comprise the step of preparing a freeze-dried formulation, and the step of preparing a freeze-dried formulation comprises: freeze-drying the final suspension. In some embodiments, the freeze-drying comprises cooling the final suspension to below −30° C. and drying the cooled final suspension below 0° C. In some embodiments, the final suspension freeze-drying comprises:

(1) pre-freezing stage, including cooling the final suspension at −45° C.;

(2) preliminary drying stage, drying the cooled final suspension below 0° C.; and (3) secondary drying stage, drying the cooled final suspension above 0° C. to obtain the ((((1r,3R,5S,7r)-3,5-dimethyladamantan-1-yl)carbamoyl)oxy)methyl benzoate freeze-dried formulation.

The present invention also provides a method for treating Alzheimer's disease in a human in need thereof, wherein the method comprises administering to the human a formulation of ((((1r,3R,5S,7r)-3,5-dimethyladamantan-1-yl)carbamoyl)oxy)methyl benzoate.

The method of the ((((1r,3R,5S,7r)-3,5-dimethyladamantan-1-yl)carbamoyl)oxy)methyl benzoate injection in the manufacture of a medicament for treating Alzheimer's disease, wherein the medicament can be injected intramuscularly or subcutaneously.

EXAMPLES

Figure 1:
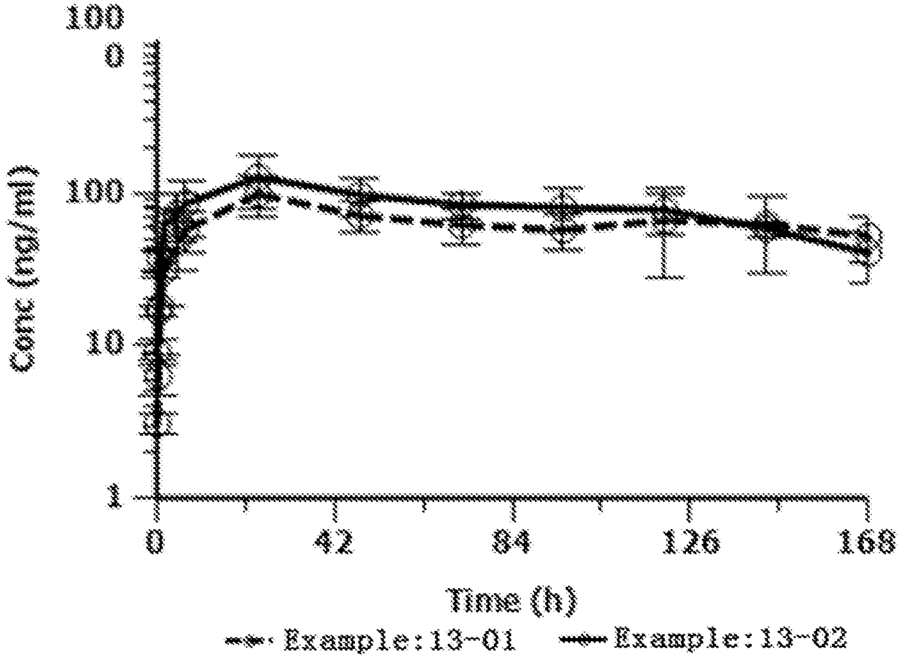
FIG. 1 shows a graph of the mean plasma concentration of memantine versus time after injecting the formulation of Example 13 of the present invention (batches 01 and 02 in Example 13) into rats.

The general method of the embodiment of the present invention is as follows:

1. ((((1r,3R,5S,7r)-3,5-dimethyladamantan-1-yl)carbamoyl)oxy)methyl benzoate suspension particle size testing instrument parameters:

instrument: Malvern Mastersizer 3000 particle size analyzer; sample injector: Hydro 3000SM(A); particle refractive index: 1.436; dispersant refractive index: 1.33; dispersant: purified water; background measurement time: 12S; sample measurement time: 10S; shading degree: 10%~20%; stirring speed: 2000 rpm; analysis model: general; measuring range: 0.005~2000 μm; particle absorption rate: 0.1; the sample was measured in triplicate to obtain an average value.

2. ((((1r,3R,5S,7r)-3,5-dimethyladamantan-1-yl)carbamoyl)oxy)methyl benzoate suspension Zeta potential detection: Malvern Nanoparticle particle size analyzer was used, the sample was taken and diluted 300 times with purified water, and the sample was measured in triplicate to obtain an average value.

3. ((((1r,3R,5S,7r)-3,5-dimethyladamantan-1-yl)carbamoyl)oxy)methyl benzoate suspension viscosity testing instrument parameters:

sample injector: modular rheometer; sample measurement time: 4 min; stirring speed: 2000 rpm; spacing between plate and sample: 0.2 mm; measuring fixture: PP-50; analysis model: general; measurement range: 0~100001/s.

4. ((((1r,3R,5S,7r)-3,5-dimethyladamantan-1-yl)carbamoyl)oxy)methyl benzoate content and related substances method:

instrument: high performance liquid chromatograph (Agilent HPLC-DAD); chromatographic column: Waters Symmetry®C8, 4.6×100 mm, 3.5 μm;

detector: UV detector, detection wavelength 210 nm; flow rate: 1.0 mL/min; mobile phase A: 1 L of ultrapure water was measured, then 1 mL of phosphoric acid was added and mixed well; mobile phase B: acetonitrile; diluent:water:acetonitrile=30:70; column temperature: 25° C.

The content/related substance gradient elution conditions were as follows, the running time was 70 min, and the injection volume was 20 μL.

| Time (min) | Phase A (%) | Phase B (%) |
|---|---|---|
| 0 | 70 | 30 |
| 10 | 5 | 95 |

-continued

| Time (min) | Phase A (%) | Phase B (%) |
|---|---|---|
| 20 | 5 | 95 |
| 20.1 | 70 | 30 |
| 25 | 70 | 30 |

5. Stability inspection, acceleration conditions: the temperature was 40° C., and the relative humidity was 75%.
6. The freeze-drying process parameters are shown in Table 1.

TABLE 1

| | | freeze-drying process parameters | | |
|---|---|---|---|---|
| | Setting temperature (° C.) | Setting time (min) | Duration (min) | Control vacuum (mbar) |
| Pre-freezing | −35 | 30 | 240 | Normal pressure |
| Primary sublimation | −10 | 100 | 3000 | 0.13 |
| Secondary sublimation | 30 | 30 | 120 | 0.13 |

Example 1: Research of Suspensions of ((((1r,3R, 5S,7r)-3,5-dimethyladamantan-1-yl)carbamoyl)oxy) methyl benzoate with Different Particle Sizes

TABLE 1-1

| | Formulation Form | | | | | | | |
|---|---|---|---|---|---|---|---|---|
| | | | | Concentration (mg/mL) | | | | |
| Component | 01 | 02 | 03 | 04 | 05 | 06 | 07 | 08 |
| ((((1r,3R,5S,7r)-3,5-dimethyladamantan-1-yl)carbamoyl)oxy) methyl benzoate | 250 | 250 | 250 | 250 | 125 | 125 | 125 | 125 |
| Tween 80 | 12 | 12 | 12 | 12 | 5.5 | 5.5 | 5.5 | 5.5 |
| Span 20 | 5 | 5 | 5 | 5 | 1.2 | 2.4 | 2.4 | 2.4 |
| Polyethylene glycol 4000 | 40 | 40 | 40 | 40 | 100 | 100 | 100 | 100 |
| Anhydrous disodium hydrogen phosphate | 1.96 | 1.96 | 1.96 | 1.96 | — | 0.983 | 0.983 | 0.983 |
| Citric acid monohydrate | 0.64 | 0.64 | 0.64 | 0.64 | — | 0.323 | 0.323 | 0.323 |

Solvent was water for injection

Preparation Process:
(1) Tween 80 and Span 20 of each batch were respectively dissolved in a purified water of about 60% of the total amount, and the solutions were stirred until completely dispersed;
(2) then polyethylene glycol 4000, anhydrous disodium hydrogen phosphate and citric acid monohydrate were added respectively, and the solutions were stirred to dissolve completely;
(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, sodium hydroxide was added to adjust the pH to 7.0-7.5, and constant volume was made;
(4) after grinding the above suspension, the particle size distribution, Zeta potential and viscosity of the suspension were measured.

Table 1-2 shows the particle size of each batch of samples, Table 1-3 shows the Zeta potential and viscosity, Table 1-4 shows the particle size under accelerated conditions for 15 days, and Table 1-5 shows the related substances under accelerated conditions for 15 days.

TABLE 1-2

| | Particle size of ((((1r,3R,5S,7r)-3,5-dimethyladamantan-1-yl)carbamoyl)oxy)methyl benzoate in suspension of each batch after grinding (unit: μm) | | | |
|---|---|---|---|---|
| Sample | Dv10 | Dv50 | Dv90 | D[4,3] |
| 01 | 2.775 | 12.246 | 56.887 | 22.883 |
| 02 | 1.827 | 6.610 | 18.727 | 9.197 |
| 03 | 1.317 | 3.788 | 9.414 | 4.714 |
| 04 | 1.153 | 3.375 | 7.428 | 3.915 |
| 05 | 0.651 | 1.605 | 5.500 | — |
| 06 | 1.652 | 5.431 | 12.799 | 6.535 |
| 07 | 1.455 | 4.200 | 10.281 | 5.193 |
| 08 | 2.322 | 8.351 | 20.381 | 10.717 |

TABLE 1-3

| Zeta potential and viscosity of each batch of suspension | | |
|---|---|---|
| Sample | Potential (mV) | Viscosity (mPa · s) |
| 01 | −39.9 | 5.01 |
| 02 | −33 | 5.23 |
| 03 | −31.3 | 5.44 |
| 04 | −27.8 | 7.18 |

TABLE 1-3-continued

| Zeta potential and viscosity of each batch of suspension | | |
|---|---|---|
| Sample | Potential (mV) | Viscosity (mPa · s) |
| 06 | −21.26 | 22.87 |
| 07 | −21.5 | 18.73 |

The results in Tables 1-2 and 1-3 show that all batches of samples with different particle sizes of ((((1r,3R,5S,7r)-3,5-dimethyladamantan-1-yl)carbamoyl)oxy)methyl benzoate are suspensions with good fluidity and good injectability. Drug particles smaller than 1 μm may have the risk of burst release, while suspension particles larger than 20 μm have problem of needle penetration during injection. According to the experimental results, it can be found that when the particle size (D50) of the prepared suspension is in the range of 1-20 μm, a suspension with better properties can be prepared.

TABLE 1-4

Research of ((((1r,3R,5S, 7r)-3,5-dimethyladamantan-1-yl)carbamoyl)oxy)methyl benzoate particle sizes in 01-04 batches suspensions under accelerated conditions for 15 days (unit: μm)

| Sample | Dv10 | Dv50 | Dv90 | D[4,3] |
|---|---|---|---|---|
| 01 | 4.355 | 16.084 | 66.538 | 30.254 |
| 02 | 2.430 | 8.620 | 23.914 | 12.010 |
| 03 | 1.590 | 4.933 | 13.299 | 6.393 |
| 04 | 1.296 | 3.941 | 12.177 | 5.531 |

TABLE 1-5

Research of related substances of ((((1r,3R,5S,7r)-3,5-dimethyladamantan-1-yl)carbamoyl)oxy)methyl benzoate in 01-04 batches suspensions under accelerated conditions for 15 days (unit: μm)

| | 0 d | | 30 d | |
|---|---|---|---|---|
| Sample | Max single impurity (%) | Total impurity (%) | Max single impurity (%) | Total impurity (%) |
| 01 | 0.03 | <LOQ | 0.03 | <LOQ |
| 02 | 0.03 | <LOQ | 0.07 | 0.08 |
| 03 | 0.03 | <LOQ | 0.03 | <LOQ |
| 04 | 0.03 | <LOQ | 0.03 | <LOQ |

The results in Tables 1-4 and 1-5 show that after 01-04 batches samples were placed under accelerated conditions for 15 days, the particle sizes and related substances of ((((1r,3R,5S,7r)-3,5-dimethyladamantan-1-yl)carbamoyl)oxy)methyl benzoate in the suspensions have no obvious change, and the stabilities are good.

Example 2: Research of ((((1r,3R,5S,7r)-3,5-dimethyladamantan-1-yl)carbamoyl)oxy)meth yl benzoate Suspension with Different Concentrations

TABLE 2-1

Formulation Form

| | Concentration (mg/mL) | | | | | | |
|---|---|---|---|---|---|---|---|
| Component | 01 | 02 | 03 | 04 | 05 | 06 | 07 |
| ((((1r,3R,5S,7r)-3,5-dimethyladamantan-1-yl)carbamoyl)oxy) methyl benzoate | 70 | 100 | 150 | 200 | 250 | 300 | 350 |
| Tween 80 | 12 | 12 | 12 | 12 | 12 | 12 | 12 |
| Span 20 | 5 | 5 | 5 | 5 | 5 | 5 | 5 |
| Polyethylene glycol 4000 | 40 | 40 | 40 | 40 | 40 | 40 | 40 |
| Anhydrous disodium hydrogen phosphate | 1.96 | 1.96 | 1.96 | 1.96 | 1.96 | 1.96 | 1.96 |
| Citric acid monohydrate | 0.64 | 0.64 | 0.64 | 0.64 | 0.64 | 0.64 | 0.64 |

Solvents are water for injection

Preparation Process:

(1) Tween 80 and Span 20 were dissolved in about 60% of a purified water of the total amount, and the solution was stirred until completely dispersed;

(2) polyethylene glycol 4000, anhydrous disodium hydrogen phosphate and citric acid monohydrate were added, and the solution was stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(4) the above suspension was ground, and the particle size distribution, Zeta potential and viscosity of the suspension were measured after grinding.

The experimental results are shown in Table 2-2 and Table 2-3.

TABLE 2-2

((((1r,3R,5S,7r)-3,5-dimethyladamantan-1-yl)carbamoyl)oxy)methyl benzoate particle size in each batch of suspension after grinding (unit: μm)

| Sample | Dv10 | Dv50 | Dv90 | D[4,3] |
|---|---|---|---|---|
| 01 | 1.237 | 3.698 | 9.670 | 4.743 |
| 02 | 1.176 | 3.429 | 8.737 | 4.326 |
| 03 | 1.073 | 2.967 | 7.199 | 3.655 |
| 04 | 1.049 | 2.811 | 6.579 | 3.403 |
| 05 | 1.058 | 2.754 | 6.209 | 3.264 |
| 06 | 1.278 | 3.489 | 7.937 | 4.142 |
| 07 | 1.326 | 3.938 | 9.466 | 4.795 |

TABLE 2-3

Zeta Potential and Viscosity of each batch of suspension

| Sample | Potential (mV) | Viscosity (mPa · s) |
|---|---|---|
| 01 | −25.9 | 2.31 |
| 02 | −29.2 | 2.48 |
| 03 | −28.7 | 3.04 |

TABLE 2-3-continued

| Zeta Potential and Viscosity of each batch of suspension | | |
|---|---|---|
| Sample | Potential (mV) | Viscosity (mPa · s) |
| 04 | −29.5 | 3.88 |
| 05 | −27.9 | 5.44 |
| 06 | −30.2 | 6.80 |
| 07 | −25.7 | 8.79 |

The results show that the suspensions with good properties can be obtained from batches 01-07. The maximum daily dose of oral memantine tablets is 20 mg, and the maximum volume of intramuscular injection is 4 mL, therefore, the theoretical minimum dose for intramuscular injection for more than 2 weeks is 280 mg; the injection volume of currently marketed long-acting intramuscular injection is less than 4 mL, therefore, the suspension content should be greater than 70 mg/mL for the theoretical dose maintained for more than 2 weeks, so batch 01 was discarded.

Example 3: Research of Suspensions with Different Stabilizers

TABLE 3-1

| Formulation Form | | | |
|---|---|---|---|
| | Concentration (mg/mL) | | |
| Component | 01 | 02 | 03 |
| ((((1r,3R,5S,7r)-3,5-dimethyladamantan-1-yl)carbamoyl)oxy)methyl benzoate | 250 | 250 | 250 |
| Tween 80 | 10 | — | — |
| Poloxamer 407 | — | 10 | — |
| 15-Hydroxystearate polyethylene glycol | — | — | 10 |

Solvents are water for injection

Preparation Process:

(1) Tween 80, poloxamer 407, 15-hydroxystearate polyethylene glycol were respectively dispersed in a purified water of about 60% of total amount, then the solutions were stirred to disperse completely;

(2) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(3) after grinding the above suspension, the particle size distribution, Zeta potential and viscosity of the suspensions were measured.

The results are shown in Table 3-2, Table 3-3.

TABLE 3-2

| ((((1r,3R,5S,7r)-3,5-dimethyladamantan-1-yl)carbamoyl)oxy)methyl benzoate particle size in each batch of suspension after grinding (unit: μm) | | | |
|---|---|---|---|
| Sample | Dv10 | Dv50 | Dv90 |
| 01 | 3.658 | 15.540 | 29.541 |
| 02 | 1.124 | 3.054 | 7.598 |
| 03 | 5.513 | 19.281 | 33.724 |

TABLE 3-3

| Zeta Potential and Viscosity of each batch of suspension after grinding | | |
|---|---|---|
| Sample | Potential (mV) | Viscosity (mPa · s) |
| 01 | −11.5 | 2.37 |
| 02 | −5.75 | 3.64 |
| 03 | 0.22 | 5.23 |

The results show that, using Tween 80, Poloxamer 407, 15-hydroxystearate polyethylene glycol as stabilizers can prepare suspensions with good properties.

Example 4: Research of Suspensions with Different Stabilizers

TABLE 4-1

| Formulation Form | | | | |
|---|---|---|---|---|
| | Concentration (mg/mL) | | | |
| Component | 01 | 02 | 03 | 04 |
| ((((1r,3R,5S,7r)-3,5-dimethyladamantan-1-yl)carbamoyl)oxy)methyl benzoate | 125 | 250 | 250 | 250 |
| Polyoxyethylene hydrogenated castor oil RH40 | — | 17 | N/A | N/A |
| Castor oil polyoxyester EL35 | — | N/A | 17 | N/A |
| Tween 80 | 5.5 | N/A | N/A | 17 |
| Span 20 | | N/A | N/A | 5 |
| Polyethylene glycol 4000 | 100 | 100 | 100 | 100 |
| Anhydrous disodium hydrogen phosphate | 0.983 | 1.96 | 1.96 | 1.96 |
| Citric acid monohydrate | 0.322 | 0.64 | 0.64 | 0.64 |

Solvent was water for injection

Preparation Process:

(1) Tween 80, polyoxyethylene hydrogenated castor oil RH40, castor oil polyoxyester EL35, the combination of Tween 80 and Span 20 were respectively dispersed in a purified water of about 60% of the total amount, and the solutions were stirred until completely dissolved;

(2) polyethylene glycol 4000, anhydrous disodium hydrogen phosphate and citric acid monohydrate were added respectively, and the solutions were stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(4) after grinding the above suspension, the particle size distribution, Zeta potential and viscosity of the suspensions were measured, and the suspensions were placed under accelerated conditions to investigate the stability.

The results show that the samples of batches 02 and 03 were viscous and had a large number of bubbles after grinding, and they could not form a flowing suspension and were not injectable, so they were discarded. The results of samples from other batches are shown in Table 4-2, Table 4-3 and Table 4-4.

TABLE 4-2

| The particle size of ((((1r,3R,5S,7r)-3,5-dimethyladamantan-1-yl)carbamoyl)oxy)methyl benzoate in each batch of suspension after grinding (unit: μm) | | | | |
|---|---|---|---|---|
| Sample | Dv10 | Dv50 | Dv90 | D[4,3] |
| 01 | 1.649 | 5.493 | 11.987 | 6.590 |
| 04 | 1.058 | 2.754 | 6.209 | 3.264 |

TABLE 4-3

| Zeta Potential and Viscosity of each batch of suspension after grinding | | |
|---|---|---|
| Sample | Potential (mV) | Viscosity mPa · s |
| 01 | −14.8 | 24.23 |
| 04 | 27.9 | 5.44 |

TABLE 4-4

| Particle size research of samples from batches 01 and 04 under accelerated conditions for 15 days (unit: μm) | | | | |
|---|---|---|---|---|
| Sample | Dv10 | Dv50 | Dv90 | D[4,3] |
| 01 | 1.441 | 4.914 | 11.266 | 5.797 |
| 04 | 1.423 | 4.782 | 17.123 | 7.320 |

The results show that when Tween 80 or the combination of Tween 80 and Span 20 was used as a stabilizer, a suspension with better properties could be prepared, and the particle size remained basically unchanged after being placed under accelerated conditions for 15 days.

Example 5: Research of Suspensions with Different Amounts of Stabilizer

TABLE 5-1

| Formulation Form | | | | | |
|---|---|---|---|---|---|
| | Concentration (mg/mL) | | | | |
| Component | 01 | 02 | 03 | 04 | 05 |
| ((((1r,3R,5S,7r)-3,5-dimethyladamantan-1-yl)carbamoyl)oxy)methyl benzoate | 125 | 125 | 125 | 125 | 125 |
| Tween 80 | 2.4 | 4 | 5.0 | 5.5 | 2.4 |
| Span 20 | 2.4 | 2.4 | 2.4 | 1.2 | 1.2 |
| Polyethylene glycol 4000 | 100 | 100 | 100 | 100 | 85 |

Solvent was water for injection

Preparation Process:

(1) Tween 80 and Span 20 of different concentrations were respectively dissolved in a purified water of about 60% of the total amount, and the solutions were stirred until completely dispersed;

(2) polyethylene glycol 4000 was added and the solutions were stirred to dissolve completely;

(3) under stirring condition, ((((1r,3R,5S,7r)-3,5-dimethyladamantan-1-yl)carbamoyl)oxy)methyl benzoate was added to give ((((1r,3R,5S,7r)-3,5-dimethyladamantan-1-yl)carbamoyl)oxy)methyl benzoate suspension, sodium hydroxide was added to adjust the pH to 7.0-7.5, and constant volume was made;

(4) after grinding the above suspension, the particle size distribution of the suspensions was measured.

During the experiment, it was found that after the samples of 05 batch were ground, the suspension was in the form of a paste, which could not form a flowing suspension and was not injectable, so it was discarded. Table 5-2 shows the results of other batches.

TABLE 5-2

| The particle size of ((((1r,3R,5S,7r)-3,5-dimethyladamantan-1-yl)carbamoyl)oxy)methyl benzoate in each batch of suspension after grinding (unit: μm) | | | |
|---|---|---|---|
| Sample | Dv10 | Dv50 | Dv90 |
| 01 | 6.635 | 15.164 | 27.725 |
| 02 | 1.538 | 4.653 | 11.090 |
| 03 | 1.472 | 4.812 | 10.270 |
| 04 | 1.013 | 2.925 | 8.302 |

The results show that the samples of batches 01-04 were suspensions with good fluidity and good injectability. Considering the safety problem after injection, the dose of stabilizer should not be too high; and when the dose of the stabilizer is too high, it will have a solubilizing effect on ((((1r,3R,5S,7r)-3,5-dimethyladamantan-1-yl)carbamoyl)oxy)methyl benzoate, which may cause burst release when injected into the body. Therefore, the concentration of the stabilizer is set from 5 mg/mL to 48 mg/mL.

Example 6: Research of Suspensions with Different Amounts of Stabilizer

TABLE 6-1

| Formulation Form | | | | | | | |
|---|---|---|---|---|---|---|---|
| | Concentration (mg/mL) | | | | | | |
| Component | 01 | 02 | 03 | 04 | 05 | 06 | 07 |
| ((((1r,3R,5S,7r)-3,5-dimethyladamantan-1-yl)carbamoyl)oxy)methyl benzoate | 125 | 125 | 125 | 250 | 250 | 250 | 250 |
| Tween 80 | 5.5 | 5.5 | 5.5 | 10 | 15 | 20 | 30 |
| Span 20 | — | 1.2 | 3.6 | 5 | 5 | 5 | 5 |

TABLE 6-1-continued

| Formulation Form | | | | | | | |
|---|---|---|---|---|---|---|---|
| | Concentration (mg/mL) | | | | | | |
| Component | 01 | 02 | 03 | 04 | 05 | 06 | 07 |
| Polyethylene glycol 4000 | 100 | 100 | 100 | 40 | 40 | 40 | 40 |
| Anhydrous disodium hydrogen phosphate | 0.983 | 0.983 | 0.983 | 1.96 | 1.96 | 1.96 | 1.96 |
| Citric acid monohydrate | 0.323 | 0.323 | 0.323 | 0.64 | 0.64 | 0.64 | 0.64 |

Solvents are water for injection

Preparation Process:

(1) Tween 80 and Span 20 of different concentrations were respectively dissolved in a purified water of about 60% of the total amount, and the solutions were stirred until completely dispersed;

(2) polyethylene glycol 4000, anhydrous disodium hydrogen phosphate and citric acid monohydrate were added, and the solution was stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(4) after grinding the above suspension, the particle size distribution, Zeta potential and viscosity of the suspensions were measured, and the related substances were detected, and the suspensions were placed in accelerated conditions to investigate the stability for 15 days and 30 days.

The particle sizes of samples of each batch are shown in Table 6-2, the Zeta potential and viscosity are shown in Table 6-3, the particle sizes under accelerated condition for 15 days are shown in Table 6-4, and the particle sizes under accelerated condition for 30 days are shown in Table 6-5.

TABLE 6-2

The particle size of ((((1r,3R,5S,7r)-3,5-dimethyladamantan-1-yl)carbamoyl)oxy)methyl benzoate in each batch of suspension after grinding (unit: μm)

| Sample | Dv10 | Dv50 | Dv90 | D[4,3] |
|---|---|---|---|---|
| 01 | 1.639 | 5.410 | 11.660 | 6.162 |
| 02 | 1.065 | 4.190 | 10.757 | 5.363 |
| 03 | 1.093 | 4.110 | 10.692 | 5.298 |
| 04 | 1.203 | 3.473 | 7.754 | 4.062 |
| 05 | 1.144 | 3.133 | 7.654 | 3.874 |
| 06 | 1.118 | 2.964 | 7.161 | 3.644 |
| 07 | 1.163 | 3.119 | 7.569 | 3.848 |

TABLE 6-3

Zeta Potential and Viscosity of each batch of suspension

| Sample | Potential (mV) | Viscosity (mPa · s) |
|---|---|---|
| 01 | −14.8 | 24.23 |
| 02 | −16.8 | 19.914 |
| 03 | −21.5 | 20.75 |
| 04 | −33.4 | 6.44 |
| 05 | −28.3 | 5.28 |
| 06 | −26.5 | 5.75 |
| 07 | −24.0 | 6.41 |

The results in Tables 6-2 and 6-3 show that the samples of 01-07 batches are suspensions with good fluidity and good injectability.

TABLE 6-4 under accelerated condition for 15 days, research on particle size of the ((((1r,3R,5S,7r)-3,5-dimethyladamantan-1-yl)carbamoyl)oxy)methyl benzoate in some batches of suspensions (unit: μm)

| Sample | Dv10 | Dv50 | Dv90 | D[4,3] |
|---|---|---|---|---|
| 03 | 1.270 | 3.755 | 9.107 | 4.629 |
| 05 | 1.405 | 4.100 | 11.732 | 5.552 |
| 06 | 1.349 | 3.802 | 10.926 | 5.194 |
| 07 | 1.357 | 3.836 | 11.095 | 5.279 |

TABLE 6-5 under accelerated condition for 30 days, research on particle size of the ((((1r,3R,5S,7r)-3,5-dimethyladamantan-1-yl)carbamoyl)oxy)methyl benzoate in some batches of suspensions (unit: μm)

| Sample | Dv10 | Dv50 | Dv90 | D[4,3] |
|---|---|---|---|---|
| 02 | 1.441 | 4.914 | 11.266 | 5.797 |
| 03 | 1.270 | 3.755 | 9.107 | 4.629 |
| 04 | 1.498 | 4.608 | 12.454 | 6.057 |

The results in Tables 6-4 and 6-5 show that after placing some batches of samples under accelerated condition for 15 days or 30 days, the particle sizes of ((((1r,3R,5S,7r)-3,5-dimethyladamantan-1-yl)carbamoyl)oxy)methyl benzoate have no obvious change, and the stabilities are good.

Example 7: Research of Suspensions with Different Suspending Agents

TABLE 7-1

Formulation Form

| Component | Concentration (mg/mL) 01 | 02 | 03 | 04 | 05 | 06 |
|---|---|---|---|---|---|---|
| ((((1r,3R,5S,7r)-3,5-dimethyladamantan-1-yl)carbamoyl)oxy) methyl benzoate | 250 | 250 | 125 | 250 | 250 | 250 |
| Tween 80 | 10 | 10 | 5.5 | 12 | 10 | 10 |
| Span 20 | 5 | 5 | 2.4 | 5 | 5 | 5 |
| Polyethylene glycol 3350 | 50 | — | — | — | — | — |
| Polyethylene glycol 4000 | — | 50 | 100 | — | — | — |
| Polyethylene glycol 1000 | — | — | — | 60 | — | — |
| Polyvinylpyrrolidone K30 | — | — | — | — | 50 | — |
| Sodium carboxymethyl cellulose 7L2P | — | — | — | — | — | 10 |
| Anhydrous disodium hydrogen phosphate | — | — | 0.983 | 1.96 | — | — |
| Citric acid monohydrate | — | — | 0.322 | 0.64 | — | — |

Solvent was water for injection

Preparation Process:

(1) Tween 80 and Span 20 were dissolved in about 60% of a purified water of the total amount, and the solution was stirred until completely dispersed;

(2) polyethylene glycol 1000, polyethylene glycol 4000, polyethylene glycol 3350, polyvinylpyrrolidone K12, sodium carboxymethyl cellulose 7L2P, anhydrous disodium hydrogen phosphate and citric acid monohydrate were added respectively, the solutions were stirred until completely dissolved;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(4) After grinding the above suspension, the particle size distribution, Zeta potential and viscosity of the suspension were measured.

During the experiment, it was found that the samples of 04 batch had many bubbles after grinding, the fluidity was not good, and the samples were not injectable, so they were discarded. The results of other batches of samples are shown in Table 7-2 and Table 7-3.

TABLE 7-2

The particle size of ((((1r,3R,5S,7r)-3,5-dimethyladamantan-1-yl)carbamoyl)oxy)methyl benzoatein each batch of suspension after grinding (unit: μm)

| Sample | Dv10 | Dv50 | Dv90 | D[4,3] |
|---|---|---|---|---|
| 01 | 2.829 | 8.457 | 17.859 | 9.705 |
| 02 | 2.738 | 12.880 | 23.892 | 13.369 |
| 03 | 1.524 | 4.641 | 11.442 | 5.750 |
| 05 | 2.742 | 10.267 | 19.376 | 10.843 |
| 06 | 2.126 | 7.429 | 17.326 | 8.737 |

TABLE 7-3

Zeta Potential and Viscosity of each batch of suspension

| Sample | Potential (mV) | Viscosity (mPa · s) |
|---|---|---|
| 01 | −23.1 | 15.06 |
| 02 | −19.1 | 4.45 |
| 03 | −22.0 | 23.7 |
| 05 | −17.2 | 7.95 |
| 06 | −22.7 | 15.10 |

The results show that when appropriate amounts of polyethylene glycol 3350, polyethylene glycol 4000, polyvinylpyrrolidone K30 or sodium carboxymethyl cellulose 7L2P were used as suspending agents, suspensions with good properties could be prepared.

Example 8: Research of the Suspensions with Different Amounts of Polyethylene Glycol 4000

TABLE 8-1

Formulation Form

| Component | Concentration (mg/mL) 01 | 02 | 03 | 04 | 05 |
|---|---|---|---|---|---|
| ((((1r,3R,5S,7r)-3,5-dimethyladamantan-1-yl)carbamoyl)oxy)methyl benzoate | 250 | 250 | 250 | 250 | 250 |
| Tween 80 | 12 | 12 | 12 | 12 | 12 |
| Span 20 | 5 | 5 | 5 | 5 | 5 |
| Polyethylene glycol 4000 | 20 | 40 | 60 | 80 | 100 |
| Anhydrous disodium hydrogen phosphate | 1.96 | 1.96 | 1.96 | 1.96 | 1.96 |
| Citric acid monohydrate | 0.64 | 0.64 | 0.64 | 0.64 | 0.64 |

Solvent was water for injection

Preparation Process:

(1) Tween 80 and Span 20 of each batch were respectively dissolved in a purified water of about 60% of the total amount, and the solutions were stirred to disperse completely;

(2) then polyethylene glycol 4000, anhydrous disodium hydrogen phosphate and citric acid monohydrate were added respectively, and the solutions were stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(4) after grinding the above suspension, the particle size distribution, Zeta potential and viscosity of the suspensions were measured, the related substances were detected, and the suspensions were placed under accelerated condition to investigate the stability.

The results of each batch of samples are shown in Table 8-2, Table 8-3, Table 8-4 and Table 8-5.

TABLE 8-2

The particle size of ((((1r,3R,5S,7r)-3,5-dimethyladamantan-1-yl)carbamoyl)oxy)methyl benzoate in each batch of suspension after grinding (unit: μm)

| Sample | Dv10 | Dv50 | Dv90 | D[4,3] |
|---|---|---|---|---|
| 01 | 1.288 | 4.191 | 12.409 | 5.367 |
| 02 | 1.058 | 2.754 | 6.209 | 3.264 |
| 03 | 1.562 | 5.099 | 11.132 | 5.813 |
| 04 | 1.155 | 3.152 | 7.626 | 3.882 |
| 05 | 1.154 | 3.085 | 7.371 | 3.775 |

TABLE 8-3

Zeta Potential and Viscosity of each batch of suspension

| Sample | Potential (mV) | Viscosity (mPa · s) |
|---|---|---|
| 01 | −29.6 | 4.54 |
| 02 | −27.9 | 5.44 |
| 03 | −29.2 | 9.58 |
| 04 | −26.6 | 8.49 |
| 05 | −26.4 | 13 |

The results in Tables 8-2 and 8-3 show that the samples of 01-05 batches are suspensions with good fluidity and good injectability.

TABLE 8-4

Research on particle size of ((((1r,3R,5S,7r)-3,5-dimethyladamantan-1-yl)carbamoyl)oxy)methyl benzoate in 02-05 batches suspensions under accelerated condition for 15 days (unit: μm)

| Sample | Dv10 | Dv50 | Dv90 | D[4,3] |
|---|---|---|---|---|
| 02 | 1.423 | 4.782 | 17.123 | 7.320 |
| 03 | 1.601 | 5.272 | 12.305 | 6.258 |
| 04 | 1.364 | 3.862 | 11.604 | 5.401 |
| 05 | 1.360 | 3.826 | 11.172 | 5.284 |

The results show that after 15 days under accelerated condition, the suspension of batch 02 with a polyethylene glycol 4000 concentration of 20 mg/mL appeared to agglomerate, and the particle sizes of the suspensions of batches 02-05 did not change significantly.

TABLE 8-5

Results of related substances in batches 02-05 under accelerated condition for 15 days

| | 0 days | | 15 days | |
|---|---|---|---|---|
| Sample | Max single impurity (%) | Total impurity (%) | Max single impurity (%) | Total impurity (%) |
| 02 | 0.03 | <LOQ | 0.03 | <LOQ |
| 03 | 0.03 | <LOQ | 0.03 | <LOQ |
| 04 | 0.03 | <LOQ | 0.02 | <LOQ |
| 05 | 0.03 | <LOQ | 0.03 | <LOQ |

The results show that after 15 days under accelerated condition, there was no significant change in related substances in batches 02-05.

Example 9: Research of Suspensions with Different pH Adjusters

TABLE 9-1

Formulation Form

| Component | Concentration (mg/mL) 01 | 02 | 03 |
|---|---|---|---|
| ((((1r,3R,5S,7r)-3,5-dimethyladamantan-1-yl)carbamoyl)oxy)methyl benzoate | 250 | 250 | 250 |
| Tween 80 | 10 | 10 | 10 |
| Span 20 | 5 | 5 | 5 |
| Polyethylene glycol 4000 | 50 | 50 | 50 |
| Anhydrous disodium hydrogen phosphate | 1.17 | 0.87 | N/A |
| Citric acid monohydrate | 0.19 | N/A | N/A |
| Sodium phosphate monohydrate | N/A | 0.54 | 1.54 |
| Sodium hydroxide | N/A | N/A | Moderate |

Solvent was water for injection

Preparation Process:

(1) Tween 80 and Span 20 of each batch were respectively dissolved in a purified water of about 60% of the total amount, and the solutions were stirred until completely dispersed;

(2) then polyethylene glycol 4000, anhydrous disodium hydrogen phosphate and citric acid monohydrate were added respectively, and the solutions were stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(4) after grinding the above suspension, the particle size distribution, Zeta potential and viscosity of the suspension were measured.

The experimental results are shown in Table 9-2 and Table 9-3.

TABLE 9-2

The particle size of ((((1r,3R,5S,7r)-3,5-dimethyladamantan-1-yl)carbamoyl)oxy)methyl benzoate in each batch of suspension after grinding (unit: μm)

| Sample | Dv10 | Dv50 | Dv90 | D[4,3] |
|---|---|---|---|---|
| 01 | 2.057 | 5.680 | 12.773 | 6.692 |
| 02 | 1.200 | 3.749 | 10.677 | 5.066 |
| 03 | 2.223 | 5.624 | 11.025 | 6.213 |

TABLE 9-3

Zeta potential and viscosity of each batch of suspension after grinding

| Sample | Potential (mV) ± SD | Viscosity (mPa · s) |
|---|---|---|
| 01 | −28.3 | 21.34 |
| 02 | −27.4 | 9.74 |
| 03 | −22.2 | 39.29 |

The results in Tables 9-2 and 9-3 show that the samples in batches 01-03 are suspensions with good fluidity and good injectability.

Example 10: Research of Suspensions with Different Amounts of pH Adjusters

TABLE 10-1

Formulation Form

| Component | Amount (g) 01 | 02 | 03 |
|---|---|---|---|
| ((((1r,3R,5S,7r)-3,5-dimethyladamantan-1-yl)carbamoyl)oxy)methyl benzoate | 250 | 250 | 250 |
| Tween 80 | 10 | 10 | 10 |
| Span 20 | 5 | 5 | 5 |
| Polyethylene glycol 4000 | 75 | 75 | 75 |
| Anhydrous disodium hydrogen phosphate | 0.585 | 2.34 | 5.85 |
| Citric acid monohydrate | 0.09 | 0.37 | 0.93 |

Solvent was water for injection

Preparation Process:

(1) Tween 80 and Span 20 of each batch were respectively dissolved in a purified water of about 60% of the total amount, and the solutions were stirred until completely dispersed;

(2) then polyethylene glycol 4000, anhydrous disodium hydrogen phosphate and citric acid monohydrate were added respectively, and the solutions were stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-7.5 and constant volume was made;

(4) after grinding the above suspension, the particle size distribution, Zeta potential and viscosity of the suspensions were measured.

The experimental results are shown in Table 10-2 and Table 10-3.

TABLE 10-2

The particle size of ((((1r,3R,5S,7r)-3,5-dimethyladamantan-1-yl)carbamoyl)oxy)methyl benzoate in each batch of suspension after grinding (unit: μm)

| Sample | Dv10 | Dv50 | Dv90 | D[4,3] |
|---|---|---|---|---|
| 01 | 3.651 | 11.213 | 22.287 | 12.208 |
| 02 | 2.314 | 8.342 | 17.789 | 9.305 |
| 03 | 1.445 | 3.629 | 7.389 | 4.085 |

TABLE 10-3

Zeta Potential and Viscosity of each batch of suspension after grinding

| Sample | Potential (mV) | Viscosity (mPa · s) |
|---|---|---|
| 01 | −18.6 | 12.40 |
| 02 | −20.1 | 18.29 |
| 03 | −20.0 | 51.98 |

Example 11: Research of Freeze-Dried Powder with Different Lyoprotectants

TABLE 11-1

Formulation Form

| Component | Concentration (mg/mL) 01 | 02 |
|---|---|---|
| ((((1r,3R,5S,7r)-3,5-dimethyladamantan-1-yl)carbamoyl)oxy)methyl benzoate | 125 | 125 |
| Tween 80 | 5.5 | 5.5 |
| Span 20 | 2.4 | 2.4 |
| Polyethylene glycol 3350 | 100 | N/A |
| Polyethylene glycol 4000 | N/A | 20.0 |
| Anhydrous disodium hydrogen phosphate | 0.98 | 0.98 |
| Citric acid monohydrate | 0.32 | 0.32 |

Solvent was water for injection

Preparation Process:

(1) Tween 80 and Span 20 of each batch were respectively dissolved in a purified water of about 60% of the total amount, and the solutions were stirred until completely dispersed;

(2) mannitol, sorbitol, glucose, sucrose, polyethylene glycol 3350, polyethylene glycol 4000 and anhydrous disodium hydrogen phosphate, citric acid monohydrate were added respectively, and the solutions were stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, sodium hydroxide was added to adjust the pH to 7.0-7.5, and constant volume was made;

(4) after grinding the above suspension, the particle size distribution of the suspensions was measured.

(5) the ground suspension was filled into a 10 mL vial with a filling volume of 5.6 mL, then freeze-dried, and the particle size, Zeta potential and viscosity of the reconstituted suspension were measured after freeze-drying. The freeze-dried formulation was placed under accelerated condition for 30 days, and the particle size and related substances of the reconstituted suspension were investigated.

The experimental results are shown in Table 11-2, Table 11-3, Table 11-4, 11-5 and Table 11-6.

TABLE 11-2

Particle size of ((((1r,3R,5S,7r)-3,5-dimethyladamantan-1-yl)carbamoyl)oxy) methyl benzoate in suspension of each batch after grinding (unit: μm)

| Sample | Dv10 | Dv50 | Dv90 | D[4,3] |
|---|---|---|---|---|
| 05 | 1.657 | 5.973 | 14.846 | 7.328 |
| 06 | 1.642 | 5.884 | 14.760 | 7.261 |

TABLE 11-3

| Particle size of ((((1r,3R,5S,7r)-3,5-dimethyladamantan-1-yl)carbamoyl)oxy)methyl benzoate in reconstituted suspension after freeze-drying (unit: μm) | | | | |
|---|---|---|---|---|
| Sample | Dv10 | Dv50 | Dv90 | D[4,3] |
| 05 | 1.700 | 5.803 | 14.238 | 7.119 |
| 06 | 1.756 | 5.989 | 14.526 | 7.505 |

TABLE 11-4

| Zeta potential and viscosity results of reconstituted suspensions after freeze-drying | | |
|---|---|---|
| Sample | Potential (mV) | Viscosity (mPa · s) |
| 06 | −28.5 | 14.9 |
| 07 | −23.7 | 19.4 |

The results show that there was no significant change in particle size between the two batches of samples before and after freeze-drying.

TABLE 11-5

| Particle size of ((((1r,3R,5S,7r)-3,5-dimethyladamantan-1-yl)carbamoyl)oxy)methyl benzoate in reconstituted suspension after the freeze-drying formulation was placed under accelerated condition for 30 days (unit: μm) | | | | |
|---|---|---|---|---|
| Sample | Dv10 | Dv50 | Dv90 | D[4,3] |
| 05 | 1.629 | 5.606 | 14.024 | 6.958 |
| 06 | 1.704 | 5.875 | 14.250 | 7.165 |

TABLE 11-6

| Results of related substances in the reconstituted suspension after the freeze-dried formulation was placed under accelerated condition for 30 days | | | | |
|---|---|---|---|---|
| | 0 days | | 30 days | |
| Sample | Max single impurity (%) | Total impurity (%) | Max single impurity (%) | Total impurity (%) |
| 05 | 0.03 | <LOQ | 0.03 | <LOQ |
| 06 | 0.03 | <LOQ | 0.04 | <LOQ |

The results show that when using polyethylene glycol 3350 or polyethylene glycol 4000 as a lyoprotectant, no process impurities were introduced into the suspension after grinding; and after the suspension was placed under accelerated condition for 30 days, the particle size and related substances of the reconstituted suspension had no obvious change.

Example 12: Research of Freeze-Dried Formulations with Different Amounts of Lyoprotectant

TABLE 12-1

| Formulation Form | | | | | |
|---|---|---|---|---|---|
| | Concentration (mg/mL) | | | | |
| Component | 01 | 02 | 03 | 04 | 05 |
| ((((1r,3R,5S,7r)-3,5-dimethyladamantan-1-yl)carbamoyl)oxy)methyl benzoate | 125 | 125 | 125 | 125 | 125 |
| Tween 80 | 5.5 | 5.5 | 5.5 | 5.5 | 5.5 |
| Span 20 | 2.4 | 2.4 | 2.4 | 2.4 | 2.4 |
| Polyethylene glycol 4000 | 60 | 80 | 90 | 100 | 125 |
| Anhydrous disodium hydrogen phosphate | 0.98 | 0.98 | 0.98 | 0.98 | 0.98 |
| Citric acid monohydrate | 0.32 | 0.32 | 0.32 | 0.32 | 0.32 |

Solvent was water for injection

Preparation Process:

(1) Tween 80 and Span 20 of each batch were respectively dissolved in a purified water of about 60% of the total amount, and the solutions were stirred until completely dispersed;

(2) polyethylene glycol 4000 and anhydrous disodium hydrogen phosphate, citric acid monohydrate were added respectively, and the solutions were stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, sodium hydroxide was added to adjust the pH to 7.0-8.0, and constant volume was made;

(4) after grinding the above suspension, the particle size distribution, Zeta potential and viscosity of the suspensions were measured.

(5) the ground suspension was filled into a 10 mL vial, the filling amount was 5.6 mL, then freeze-dried, and the particle size of the reconstituted suspension after freeze-drying was measured; then the freeze-dried formulation was placed under accelerated condition for 30 days, the particle size and related substances of the reconstituted suspension of the freeze-dried formulation were investigated.

The experimental results are shown in Table 12-2, Table 12-3, Table 12-4, Table 12-5 and Table 12-6.

TABLE 12-2

The particle size of ((((1r,3R,5S,7r)-3,5-dimethyladamantan-1-yl)carbamoyl)oxy)methyl benzoate in each batch of suspension after grinding (unit: μm)

| Sample | Dv10 | Dv50 | Dv90 | D[4,3] |
|---|---|---|---|---|
| 01 | 1.237 | 3.659 | 10.103 | 4.864 |
| 02 | 0.984 | 2.832 | 8.038 | 3.827 |
| 03 | 1.317 | 4.417 | 12.918 | 5.964 |
| 04 | 1.642 | 5.884 | 14.760 | 7.261 |
| 05 | 1.354 | 4.289 | 12.367 | 5.773 |

TABLE 12-3

Zeta potential and viscosity results of each batch of suspension after grinding

| Sample | Potential (mV) | Viscosity (mPa · s) |
|---|---|---|
| 01 | −23.7 | 10.3 |
| 02 | −24.5 | 15.4 |
| 03 | −25.3 | 14.3 |
| 04 | −28.9 | 19.4 |
| 05 | −24.9 | 20.6 |

TABLE 12-4

Particle size of ((((1r,3R,5S,7r)-3,5-dimethyladamantan-1-yl)carbamoyl)oxy)methyl benzoate in reconstituted suspension after freeze-drying (unit: μm)

| Sample | Dv10 | Dv50 | Dv90 | D[4,3] |
|---|---|---|---|---|
| 01 | 1.372 | 4.354 | 13.999 | 7.007 |
| 02 | 1.216 | 3.463 | 9.693 | 4.712 |
| 03 | 1.402 | 4.323 | 11.689 | 5.616 |
| 04 | 1.756 | 5.989 | 14.526 | 7.505 |
| 05 | 1.476 | 4.269 | 10.984 | 5.437 |

The results show that there was no significant change in particle size of the 01-05 batch samples before and after freeze-drying.

TABLE 12-5

Particle size of ((((1r,3R,5S,7r)-3,5-dimethyladamantan-1-yl)carbamoyl)oxy)methyl benzoate in reconstituted suspension after the freeze-drying formulation was placed under accelerated condition for 30 days (unit: μm)

| Sample | Dv10 | Dv50 | Dv90 | D[4,3] |
|---|---|---|---|---|
| 02 | 1.072 | 2.883 | 7.074 | 3.601 |
| 03 | 1.227 | 3.576 | 9.738 | 4.716 |
| 04 | 1.704 | 5.875 | 14.25 | 7.165 |
| 05 | 1.361 | 3.915 | 9.869 | 4.950 |

TABLE 12-6

Results of related substances in the reconstituted suspension after the freeze-dried formulation was placed under accelerated condition for 30 days

| | 0 days | | 30 days | |
|---|---|---|---|---|
| Sample | Max single impurity (%) | Total impurity (%) | Max single impurity (%) | Total impurity (%) |
| 02 | 0.03 | <LOQ | 0.03 | <LOQ |
| 03 | 0.03 | <LOQ | 0.03 | <LOQ |
| 04 | 0.03 | <LOQ | 0.04 | <LOQ |
| 05 | 0.03 | <LOQ | 0.04 | <LOQ |

The results show that no process impurities were introduced after grinding the suspensions in batches 02-05; and after the suspensions were placed under accelerated condition for 30 days, the particle size and related substances of the reconstituted suspensions did not change significantly.

Example 13: Pharmacokinetic study of ((((1r,3R,5S,7r)-3,5-dimethyladamantan-1-yl)carbamoyl)oxy)methyl benzoate injection formulation in rats

TABLE 13-1

Formulation Form

| | Concentration (mg/mL) | |
|---|---|---|
| Component | 01 | 02 |
| ((1r,3R,5S,7r)-3,5-dimethyladamantan-1-yl)carbamoyl)oxy)methyl benzoate | 125 | 125 |
| Tween 80 | 5.5 | 5.5 |
| Span 20 | 2.4 | 2.4 |
| Polyethylene glycol 4000 | 100 | 100 |
| Anhydrous disodium hydrogen phosphate | 0.49 | 0.49 |
| Citric acid monohydrate | 0.16 | 0.16 |

Solvent was water for injection

Preparation Process:

(1) Tween 80 and Span 20 of each batch were respectively dissolved in a purified water of about 60% of the total amount, and the solutions were stirred until completely dispersed;

(2) polyethylene glycol 4000 and anhydrous disodium hydrogen phosphate, citric acid monohydrate were added respectively, and the solutions were stirred to dissolve completely;

(3) under stirring condition, ((((1r,3R,5S,7r)-3,5-dimethyladamantan-1-yl)carbamoyl)oxy)methyl benzoate was slowly added to give ((((1r,3R,5S,7r)-3,5-dimethyladamantan-1-yl)carbamoyl)oxy)methyl benzoate suspension, the pH was adjusted to 7.0-8.0 and constant volume was made;

(4) after grinding the above suspension, the particle size distribution of the suspensions was measured.

(5) the ground suspension was filled into a 10 mL vial with a filling volume of 5.6 mL, then freeze-dried, and the particle size of the reconstituted suspension of the freeze-dried formulation was measured.

The experimental results are shown in Table 13-2 and Table 13-3.

TABLE 13-2

| | Particle size of ((((1r,3R,5S,7r)-3,5-dimethyladamantan-1-yl)carbamoyl)oxy)methyl benzoate in suspension before freeze-drying (unit: μm) | | | |
|---|---|---|---|---|
| Sample | Dv10 | Dv50 | Dv90 | D[4,3] |
| 01 | 1.307 | 3.913 | 11.290 | 5.327 |
| 02 | 0.974 | 2.724 | 7.021 | 3.503 |

TABLE 13-3

| | Particle size of ((((1r,3R,5S,7r)-3,5-dimethyladamantan-1-yl)carbamoyl)oxy)methyl benzoate in suspension after freeze-drying and reconstitution (unit: μm) | | | |
|---|---|---|---|---|
| Sample | Dv10 | Dv50 | Dv90 | D[4,3] |
| 01 | 1.626 | 4.907 | 11.842 | 6.041 |
| 02 | 1.268 | 3.483 | 8.135 | 4.259 |

The results show that the particle sizes of the suspension before freeze-drying and the suspension after freeze-drying and reconstitution were very close.

Pharmacokinetic studies in rats using batches 01 and 02: 75 mg/kg of ((((1r,3R,5S,7r)-3,5-dimethyladamantan-1-yl)carbamoyl)oxy)methyl benzoate suspension aqueous solution was administrated by intramuscular injection, whole blood was collected at 0.25 h, 1 h, 2 h, 5 h, 7 h, 24 h, 48 h, 72 h, 96 h, 120 h, 140 h and 170 h before and after administration; then the whole blood was centrifuged at 12,000 rpm for 2 min to separate plasma, and the plasma was stored at –20° C. or –70° C. until LC/MS/MS analysis.

The parameters for LC/MS/MS are as follows:

TABLE 13-4

| | |
|---|---|
| Multiple reaction detection scan | 299.1→150 |
| Fragmentation voltage | 25 V |
| Capillary voltage | 4000 V |
| Dryer temperature | 350° C. |
| Atomizer | 40 psi |
| Flow rate of dryer | 9 L/min |

Analysis was performed using a Waters Xbridge C18, 2.1×50 mm, 2.7 μM column, 20 μL of sample was injected. Analytical conditions: mobile phase was 2 mM ammonium formate+0.1% formic acid (A) and methanol+2 mM ammonium formate+0.1% formic acid (B). The flow rate was 0.4 mL/min.

The mobile phase gradient is shown in Table 13-5:

TABLE 13-5

| Time | Mobile phase gradient |
|---|---|
| 0.5 min | 10% |
| 1.0 min | 85% |
| 2.7 min | 85% |
| 2.71 min | 10% |
| 4.0 min | stop |

Table 13-6 shows the pharmacokinetic data of the formulation of Example 13 in rats. The compounds of the present invention have good pharmacokinetic properties. The average drug-time curve of in vivo after intramuscular injection in rats is shown in FIG. 1.

As can be seen from FIG. 1, after administration of ((((1r,3R,5S,7r)-3,5-dimethyladamantan-1-yl)carbamoyl)oxy)methyl benzoate suspension, the drug is continuously slowly released and can be maintained within a certain concentration range. The ((((1r,3R,5S,7r)-3,5-dimethyladamantan-1-yl)carbamoyl)oxy)methyl benzoate suspension prepared herein has a significant sustained release effect within 1 week or at least 1 week.

TABLE 13-6

| | | | | Pharmacokinetic data in rats | | | |
|---|---|---|---|---|---|---|---|
| Sample | Dosage form | Dosage | Rat sex | Exposure $AUC_{last}$ (h * ng/mL) | Peak concentration $C_{max}$ (ng/mL) | Half life $T_{1/2}$ (h) | Peak time $T_{max}$ (h) |
| Example 13-01 | Suspension | 75 mg/kg | Male | 11000 | 98 | 186 | 24 |
| Example 13-02 | Suspension | 75 mg/kg | Male | 13700 | 127 | 132 | 24 |

Example 14: Pharmacokinetic Study of ((((1r,3R,5S,7r)-3,5-dimethyladamantan-1-yl)carbamoyl)oxy)methyl benzoate Injection Formulation in Rats and Dogs

TABLE 14-1

| | Formulation Form |
|---|---|
| Material name | Formulation content (mg/mL) |
| ((((1r,3R,5S,7r)-3,5-dimethyladamantan-1-yl)carbamoyl)oxy)methyl benzoate (main drug) | 125 |
| Tween 80 | 5.5 |
| Span 20 | 2.4 |
| Polyethylene glycol 4000 | 100 |
| Disodium phosphate | 0.983 |
| Citric acid monohydrate | 0.323 |
| Water for injection | |

Preparation method: Tween 80 and Span 20 were dissolved in a water for injection of about 60% of the total amount, the solution was stirred until completely dispersed; then polyethylene glycol 4000 and anhydrous disodium hydrogen phosphate, citric acid monohydrate were added, the solution was stirred until completely dissolved; under stirring conditions, ((((1r,3R,5S,7r)-3,5-dimethyladamantan-1-yl)carbamoyl)oxy)methyl benzoate was slowly added to give a ((((1r,3R,5S,7r)-3,5-dimethyladamantan-1-yl)carbamoyl)oxy)methyl benzoate suspension and constant volume was made; after grinding the above suspension, it was filled into a 10 mL vial with a filling volume of 5.6 mL, and freeze-dried.

The obtained freeze-dried powder was reconstituted with water and the particle size was measured. The particle size results were as follows: Dv10 was 1.516 μm, Dv50 was 4.731 μm, Dv90 was 11.953 μm, Dv99 was 33.017 μm, Dv4,3 was 6.290 μm; the content was 115%.

Figure 2:
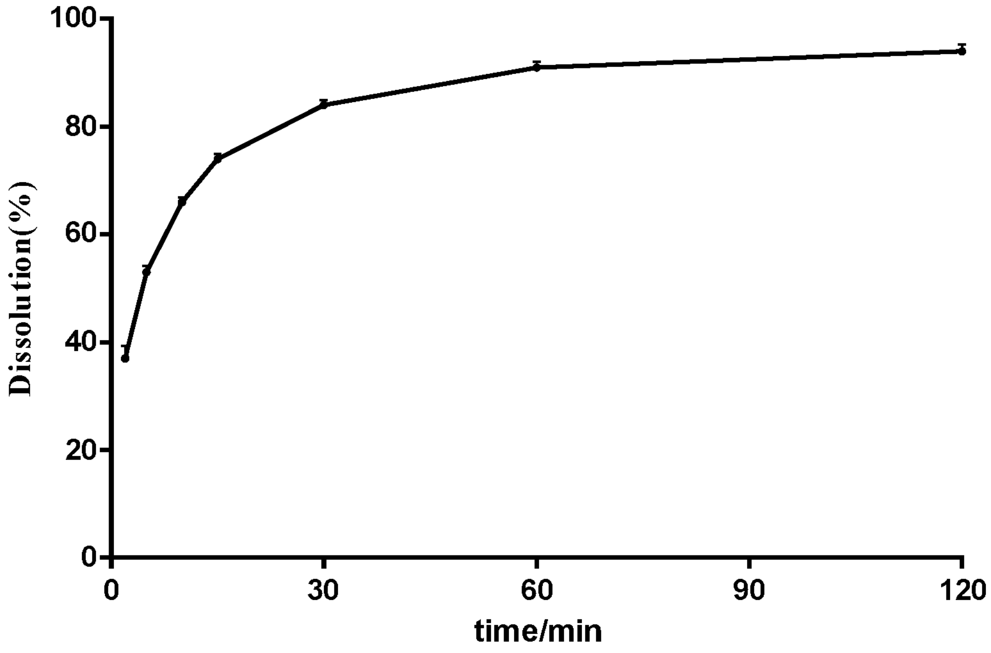
FIG. 2 is the in vitro dissolution profile of the sample of Example 13.

The freeze-dried powder obtained in Example 14 was reconstituted with 2.4 g of water and then the mixture was subjected to an in vitro dissolution test. The dissolution method was paddle method, the dissolution medium was 0.5% sodium dodecyl sulfate solution, the rotation speed was 50 rpm, and the temperature was 30° C. The in vitro dissolution profile is shown in FIG. 2.

The lyophilized formulation in Example 14 was reconstituted with 2.4 g of water for injection to obtain a ((((1r, 3R,5S,7r)-3,5-dimethyladamantan-1-yl)carbamoyl)oxy) methyl benzoate suspension with concentration of 200 mg/mL, the suspension was used for in vivo pharmacokinetic studies in rats and dogs. Memantine hydrochloride and water for injection were formulated into 2.0 mg/mL and 4.0 mg/mL solutions for oral gavage as the control group. The dose groups for rats and dogs are shown in Table 14-2 and Table 14-3 respectively, there are 8 rats in each group, half male and female, and 10 dogs in each group, half male and female.

Blood Sampling Time Points:

Example 14-01/14-02/14-06/14-07: 0.5 h, 1 h, 2 h, 4 h, 6 h, 8 h, 24 h before and after administration;

Example 14-03/14-04/14-05/14-08/14-09/14-10: 1 h, 4 h, 8 h, 24 h, 48 h, 72 h, 96 h, 120 h, 144 h, 192 h, 264 h, 312 h before and after administration.

Blood Sample Testing Method:

100 μL of Protease Inhibitor Cocktail (20×) was added to per 1 mL of whole blood, the mixture was inverted up and down to mix well, the whole blood sample was placed in an ice bath before centrifugation, then centrifuged at 4° C. for 10 minutes at 1800×g within 1 hour, and the plasma was separated in an ice bath. The concentration of active compound 1-amino-3,5-dimethyladamantanamine in blood sample at each time point was detected by LC-MS/MS method. The LC/MS/MS system used for analysis included an LC-30 ultra-high performance liquid chromatograph and a Qtrap-5500 ion hydrazine mass spectrometer, the temperature of dryer was 550° C., the flow rate of drying gas was 9 L/min, and the pressure of nebulizer was 40 psi Capillary voltage 3500 V. Quantitative analysis was performed in MRM mode, and the parameters of MRM conversion were shown in Table 14-4. The analysis was performed using a Waters Xbridge C18, 2.1×50 mm, 2.7 UM column, 1 μL of sample was injected. Analytical conditions: The mobile phase was 0.1% formic acid (A) and methanol (B). The flow rate was 0.45 mL/min. The mobile phase gradients are shown in Table 14-5.

TABLE 14-2

Schedule of rat dosing

| No. | Dosing samples | Route of administration | Dosage (mg/kg) | Dosing concentration (mg/mL) | Dosing volume (mL/kg) |
|---|---|---|---|---|---|
| Example 14-01 | Memantine hydrochloride solution | Oral gavage | 20 | 2 | 10 |
| Example 14-02 | Memantine hydrochloride solution | Oral gavage | 40 | 4 | 10 |
| Example 14-03 | ((((1r,3R,5S,7r)-3,5-dimethyladamantan-1-yl)carbamoyl)oxy)methyl benzoate suspension | Intramuscular injection | 140 | 200 | 0.7 |
| Example 14-04 | ((((1r,3R,5S,7r)-3,5-dimethyladamantan-1-yl)carbamoyl)oxy)methyl benzoate suspension | Intramuscular injection | 280 | 200 | 1.4 |
| Example 14-05 | ((((1r,3R,5S,7r)-3,5-dimethyladamantan-1-yl)carbamoyl)oxy)methyl benzoate suspension | Intramuscular injection | 560 | 200 | 2.8 |

TABLE 14-3

Schedule of dog dosing

| No. | Dosing samples | Route of administration | Dosage (mg/kg) | Dosing concentration (mg/mL) | Dosing volume (mL/kg) |
|---|---|---|---|---|---|
| Example 14-06 | Memantine hydrochloride solution | Oral gavage | 7.5 | 2 | 3.75 |
| Example 14-07 | Memantine hydrochloride solution | Oral gavage | 15 | 4 | 3.75 |
| Example 14-08 | ((((1r,3R,5S,7r)-3,5-dimethyladamantan-1-yl)carbamoyl)oxy)methyl benzoate suspension | Intramuscular injection | 50 | 200 | 0.25 |
| Example 14-09 | ((((1r,3R,5S,7r)-3,5-dimethyladamantan-1-yl)carbamoyl)oxy)methyl benzoate suspension | Intramuscular injection | 100 | 200 | 0.5 |
| Example 14-10 | ((((1r,3R,5S,7r)-3,5-dimethyladamantan-1-yl)carbamoyl)oxy)methyl benzoate suspension | Intramuscular injection | 200 | 200 | 1.0 |

TABLE 14-4

| MRM Parameters of Mass Spectrometer | | | | | |
|---|---|---|---|---|---|
| Analyte | Q1(m/z) | Q3(m/z) | DP(v) | CE(v) | Dwell time(ms) |
| Memantine | 180.2 | 163 | 90 | 22 | 100 |
| Memantine Internal Standard | 186.2 | 169.2 | 90 | 22 | 100 |

TABLE 14-5

| Mobile Phase Gradients | |
|---|---|
| Time | Gradients of Mobile Phase B |
| 0.5 min | 20% |
| 1 min | 85% |

TABLE 14-5-continued

| Mobile Phase Gradients | |
|---|---|
| Time | Gradients of Mobile Phase B |
| 2.4 min | 85% |
| 2.5 min | 20% |
| 2.8 min | 20% |
| 3.2 min | 85% |
| 4.2 min | 85% |
| 4.3 min | 20% |
| 4.8 min | 20% |

Figure 3:
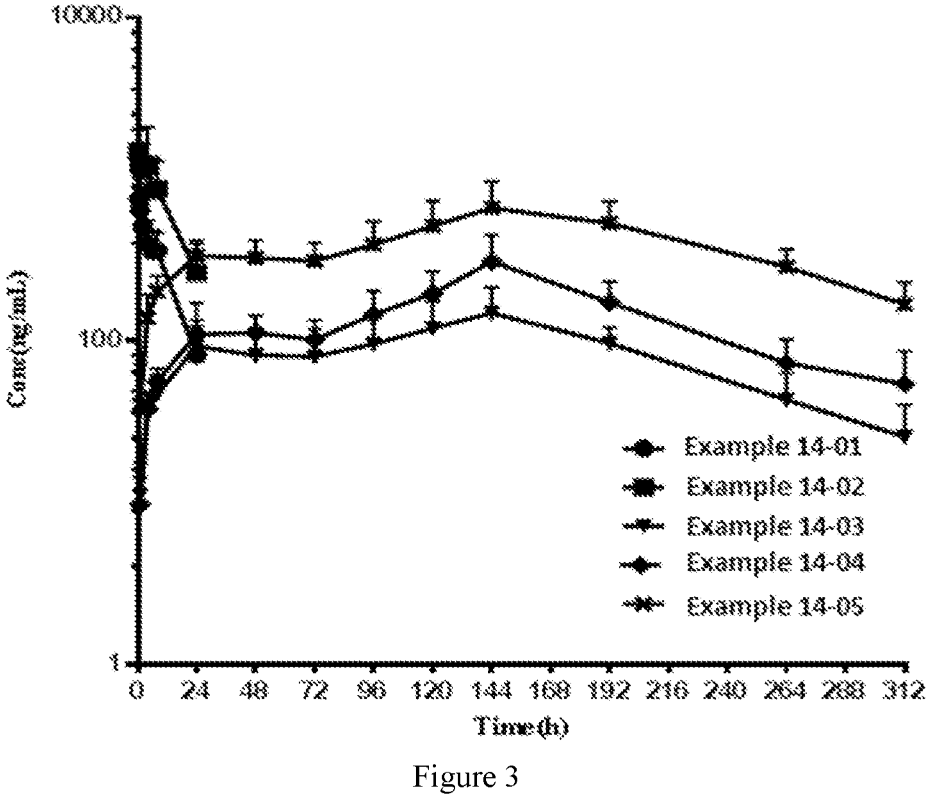
FIG. 3 shows a graph of the mean plasma concentration of memantine versus time after injecting the formulation of Example 14 of the present invention (batches 01-05 in Example 14) into rats.
Figure 4:
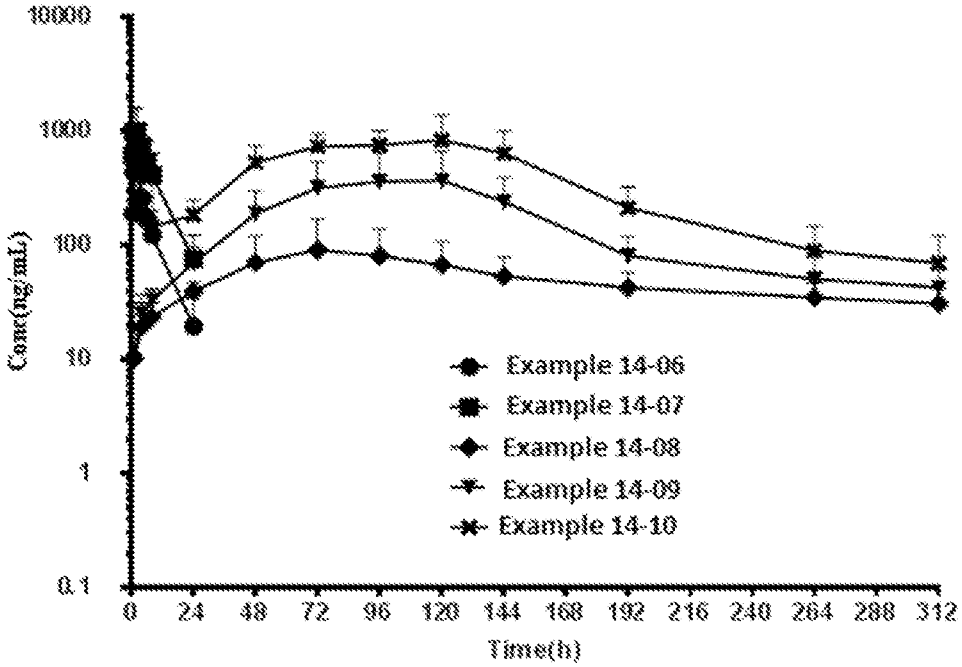
FIG. 4 shows a graph of the mean plasma concentration of memantine versus time after injecting the formulation of Example 14 of the present invention (batches 06-10 in Example 14) into dogs.

The plasma concentration time curve after administration in rats is shown in FIG. 3, and the pharmacokinetic data are shown in Table 14-6; the plasma concentration time curve after administration in dogs is shown in FIG. 4, and the pharmacokinetic data are shown in Table 14-7.

TABLE 14-6

Pharmacokinetic data of memantine in rats after a single dose

| Groups (Concentration) | | Example 14-01 | Example 14-02 | Example 14-03 |
|---|---|---|---|---|
| Cmax(ng/mL) | Female | 911 ± 412 | 2010 ± 750 | 186 ± 67.4 |
| | Male | 624 ± 176 | 1190 ± 592 | 115 ± 42.8 |
| Tmax(h) | Female | 0.63 ± 0.25 | 1.4 ± 1.8 | 140 ± 39 |
| | Male | 0.5 ± 0.0 | 0.50 ± 0.0 | 140 ± 0.0 |
| AUClast | Female | 9039.375 ± 781.341 | 22268.125 ± 7393.291 | 31947.690 ± 4427.470 |
| (h * ng/mL) | Male | 5066.050 ± 934.921 | 12463.000 ± 5211.482 | 19876.668 ± 5441.918 |

| Groups (Concentration) | | Example 14-04 | Example 14-05 |
|---|---|---|---|
| Cmax(ng/mL) | Female | 261 ± 182 | 665 ± 285 |
| | Male | 360 ± 91.0 | 808 ± 314 |
| Tmax(h) | Female | 110 ± 60 | 160 ± 24 |
| | Male | 140 ± 0.0 | 130 ± 14 |
| AUClast | Female | 43331.293 ± 17176.435 | 43615.143 ± 4268.905 |
| (h * ng/mL) | Male | 129964.163 ± 28154.851 | 117330.113 ± 38271.303 |

TABLE 14-7

Pharmacokinetic data of Memantine in dogs after a single dose

| Groups (Concentration) | | Example 14-06 | Example 14-07 | Example 14-08 |
|---|---|---|---|---|
| Cmax | Female | 625 ± 316 | 1270 ± 402 | 101 ± 104 |
| (ng/mL) | Male | 560 ± 279 | 1210 ± 698 | 90.5 ± 54.7 |
| Tmax | Female | 1.3 ± 0.67 | 1.9 ± 1.3 | 72 ± 29 |
| (h) | Male | 1.2 ± 0.45 | 1.7 ± 1.4 | 110 ± 50 |
| AUClast | Female | 3421.133 ± 1834.683 | 9961.720 ± 1130.991 | 14213.898 ± 4442.371 |
| (h * ng/mL) | Male | 3569.858 ± 1725.232 | 10712.800 ± 6421.818 | 17513.986 ± 5778.648 |

TABLE 14-7-continued

| Pharmacokinetic data of Memantine in dogs after a single dose | | | |
|---|---|---|---|
| Groups (Concentration) | | Example 14-09 | Example 14-10 |
| Cmax | Female | 481 ± 338 | 1170 ± 936 |
| (ng/mL) | Male | 255 ± 240 | 1050 ± 413 |
| Tmax | Female | 110 ± 27 | 72 ± 44 |
| (h) | Male | 91 ± 31 | 110 ± 27 |
| AUClast | Female | 54335.063 ± 25108.22 | 96692.272 ± 34533.326 |
| (h * ng/mL) | Male | 39952.488 ± 17968.732 | 128228.646 ± 34694.644 |

From the above pharmacokinetic data of rats and dogs, it can be found that: the dosage of oral administration is much lower than that of intramuscular injection, and the Cmax of oral administration is still much larger than that of intramuscular injection, after oral administration, the plasma concentration peaked rapidly and then decreased rapidly. The ((((1r,3R,5S,7r)-3,5-dimethyladamantan-1-yl)carbamoyl)oxy)methyl benzoate injection formulation provided herein can maintain the plasma concentration above the oral administration trough concentration for at least 2 weeks, indicating that the long-acting intramuscular injection formulation can avoid the "peak-trough" phenomenon of the plasma concentration, and can reduce the dosing frequency to every two once a week.

Reference throughout this specification to "some embodiments", "some implementations", "a specific example" or "some examples" means that a particular feature, structure, material, or characteristic described in connection with the embodiment or example is included in at least one embodiment or example of the present disclosure. In various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A ((((1r,3R,5S,7r)-3,5-dimethyladamantan-1-yl)carbamoyl)oxy)methyl benzoate formulation, wherein the Dv50 of the ((((1r,3R,5S,7r)-3,5-dimethyladamantan-1-yl)carbamoyl)oxy)methyl benzoate in the formulation is 1.0 μm-20.0 μm, wherein the ((((1r,3R,5S,7r)-3,5-dimethyladamantan-1-yl)carbamoyl)oxy)methyl benzoate has a concentration of 105.0 mg/mL-300.0 mg/mL, and the formulation further comprises:

a stabilizer having a concentration of 5.0 mg/mL-48.0 mg/mL, wherein the stabilizer comprises at least one selected from Polysorbate 80, sorbitan monolaurate, poloxamer 407, and 15-hydroxystearate polyethylene glycol.

2. The formulation of claim 1, wherein the stabilizer is selected from (i) Polysorbate 80 and (ii) a combination of Polysorbate 80 and sorbitan monolaurate.

3. The formulation of claim 1, further comprising a suspending agent, the concentration of the suspending agent is 0.35 mg/mL-125.0 mg/mL.

4. The formulation of claim 3, wherein the suspending agent comprises at least one selected from polyethylene glycol 4000, polyethylene glycol 3350, sodium carboxymethyl cellulose, and polyvinylpyrrolidone.

5. The formulation of claim 1, further comprising a pH adjuster, the pH adjuster comprises at least one selected from hydrochloric acid, sodium hydroxide, phosphoric acid and its salts, tartaric acid and its salts, acetic acid and its salts, citric acid and its salts, carbonic acid and its salts.

6. The formulation of claim 1, further comprising water for injection.

7. The formulation of claim 1, optionally comprising water for injection, wherein the formulation continues to release memantine for at least 1 week after the injection.

8. The formulation of claim 1, wherein:

the stabilizer is selected from (i) Polysorbate 80 and (ii) a combination of Polysorbate 80 and sorbitan monolaurate; and the formulation further comprises a suspending agent, wherein the suspending agent is polyethylene glycol 4000.

9. The formulation of claim 1, wherein the stabilizer is selected from (i) Polysorbate 80 and (ii) a combination of Polysorbate 80 and sorbitan monolaurate, and wherein the formulation further comprises:

a suspending agent selected from polyethylene glycol 4000, polyethylene glycol 3350, sodium carboxymethyl cellulose and polyvinylpyrrolidone, wherein the concentration of the suspending agent is 0.35 mg/mL-125.0 mg/mL; and, optionally a pH adjuster.

10. The formulation of claim 1, comprising:

(a) ((((1r,3R,5S,7r)-3,5-dimethyladamantan-1-yl)carbamoyl)oxy)methyl benzoate with the concentration of 125.0 mg/mL-250.0 mg/mL;

(b) a combination of Polysorbate 80 and sorbitan monolaurate with the concentration of 5.0 mg/mL-25.0 mg/mL; and/or (c) polyethylene glycol 4000 with the concentration of 50.0 mg/mL-120.0 mg/mL;

optionally comprising a pH adjuster.

11. The formulation of claim 1, wherein the concentration of ((((1r,3R,5S,7r)-3,5-dimethyladamantan-1-yl)carbamoyl)oxy)methyl benzoate is 125.0 mg/mL.

12. The formulation of claim 1, comprising:

(a) ((((1r,3R,5S,7r)-3,5-dimethyladamantan-1-yl)carbamoyl)oxy)methyl benzoate with the concentration of 125.0 mg/mL;

(b) a combination of Polysorbate 80 and sorbitan monolaurate with the concentration of 8.0 mg/mL; and (c) polyethylene glycol 4000 with the concentration of 100.0 mg/mL.

13. The formulation of claim 1, the pH is 6.0-9.0.

14. The formulation of claim 1, after the injection, the formulation continues to release memantine for at least 1 week.

15. The formulation of claim 1, which is a ready-to-use liquid injection or a freeze-dried formulation.

16. A method of preparing the formulation of claim 1, comprising the following steps:

(a) mixing the stabilizer and water, optionally, adding a suspending agent;

(b) adding ((((1r,3R,5S,7r)-3,5-dimethyladamantan-1-yl) carbamoyl)oxy)methyl benzoate to obtain a suspension;

(c) optionally, adjusting pH with a pH adjuster and then making constant volume;

(d) grinding the above suspension to obtain the final suspension.

17. The method of claim 16, further comprising the step of preparing a freeze-dried formulation, which comprises: freeze-drying the final suspension.

18. A method for treating Alzheimer's disease in a human in need thereof, wherein the method comprises administering to the human a formulation of claim 1.

19. A ((((1r,3R,5S,7r)-3,5-dimethyladamantan-1-yl)carbamoyl)oxy)methyl benzoate formulation, wherein the Dv50 of the ((((1r,3R,5S,7r)-3,5-dimethyladamantan-1-yl) carbamoyl)oxy)methyl benzoate in the formulation is 1.0 μm-20.0 μm.

20. The formulation of claim 19, further comprising a stabilizer, wherein the concentration of the stabilizer is 5.0 mg/mL-48.0 mg/mL.

* * * * *